(12) United States Patent
Kramer et al.

(10) Patent No.: US 9,289,619 B2
(45) Date of Patent: Mar. 22, 2016

(54) TIMING CYCLES FOR SYNCHRONIZED MULTISITE CARDIAC PACING

(75) Inventors: Andrew Kramer, Stillwater, MN (US); Jeff Stahmann, Ramesy, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1592 days.

(21) Appl. No.: 11/894,100

(22) Filed: Aug. 20, 2007

(65) Prior Publication Data

US 2008/0046057 A1 Feb. 21, 2008

Related U.S. Application Data

(62) Division of application No. 10/270,035, filed on Oct. 11, 2002, now Pat. No. 7,260,432.

(60) Provisional application No. 60/328,872, filed on Oct. 11, 2001.

(51) Int. Cl.
*A61N 1/39* (2006.01)
*A61N 1/362* (2006.01)

(52) U.S. Cl.
CPC ............ *A61N 1/3956* (2013.01); *A61N 1/3622* (2013.01)

(58) Field of Classification Search
CPC .......................... A61N 1/3656; A61N 1/3622
USPC ......... 600/373, 374, 393, 508, 515, 516, 518, 600/519, 521, 509; 607/4, 5, 9, 14, 25, 116, 607/119, 122, 123
See application file for complete search history.

(56) References Cited

U.S. PATENT DOCUMENTS

| 4,928,688 | A | 5/1990 | Mower |
| 5,643,326 | A | 7/1997 | Weiner et al. |
| 5,983,138 | A | 11/1999 | Kramer |
| 6,282,447 | B1 | 8/2001 | Cook et al. |
| 6,285,907 | B1 | 9/2001 | Kramer et al. |
| 6,345,201 | B1 * | 2/2002 | Sloman et al. ................. 607/28 |
| 6,421,564 | B1 | 7/2002 | Yerich et al. |
| 6,456,878 | B1 | 9/2002 | Yerich et al. |
| 6,466,820 | B1 * | 10/2002 | Juran et al. ........................ 607/9 |

(Continued)

OTHER PUBLICATIONS

Aaronson KD, Schwartz S, Chen T-M, Wong K-L, Goin JE, Mancini DM. Development and prospective validation of a clinical index to predict survival in ambulatory patients referred for cardiac transplant evaluation. Circulation 1997; 95: 2660-7.

(Continued)

*Primary Examiner* — Amanda Patton
(74) *Attorney, Agent, or Firm* — Schwegman Lundberg & Woessner, P.A.

(57) ABSTRACT

The present invention relates to identifying and using groups of cardiac events associated with depolarization wavefronts to coordinate the delivery of pacing therapy to the heart. According to one aspect of the invention, cardiac events associated with a plurality of cardiac sites are detected. The cardiac sites may be located in a single heart chamber or in bilateral heart chambers. A group of detected cardiac events associated with a depolarization wavefront is identified. According to another aspect of the invention, a particular cardiac event of an identified group associated with a depolarization wavefront may be used to synchronize pacing therapy delivered to the heart. According to yet another aspect, premature ventricular contractions may be classified using the identified groups.

11 Claims, 35 Drawing Sheets

(56) References Cited

U.S. PATENT DOCUMENTS

| | | |
|---|---|---|
| 6,477,415 B1 | 11/2002 | Yerich et al. |
| 6,493,730 B1 | 12/2002 | Lewis et al. |
| 6,496,730 B1 | 12/2002 | Kleckner et al. |
| 6,501,987 B1 | 12/2002 | Lovett et al. |
| 6,501,988 B2 | 12/2002 | Kramer et al. |
| 6,512,952 B2 | 1/2003 | Stahmann et al. |
| 6,522,921 B2 | 2/2003 | Stahmann et al. |
| 6,553,258 B2 | 4/2003 | Stahmann et al. |
| 6,553,259 B2 * | 4/2003 | Mouchawar et al. ............ 607/11 |
| 6,564,097 B1 | 5/2003 | Williams et al. |
| 6,609,028 B2 | 8/2003 | Struble |
| 2002/0082653 A1 | 6/2002 | Stahmann et al. |
| 2002/0082654 A1 | 6/2002 | Kramer et al. |
| 2002/0082655 A1 | 6/2002 | Kramer et al. |

OTHER PUBLICATIONS

Abraham WT. Rationale and design of a randomized clinical trial to assess the safety and efficacy of cardiac resynchronization therapy in patients with advanced heart failure: the Multicenter InSync Randomized Clinical Evaluation (MIRACLE). J Card Fail Dec. 2000;6(4):369-80, Abstract only.

Askenazi, J., J.H. Alexander, D.I. Koenigsberg, N. Belie, and M. Lesch. 1984. Alteration of left ventricular performance by left bundle branch block simulated with atrioventricular sequential pacing. *Am J Cardiol* 53:99-104, Abstract only.

Auricchio A, Ding J, Yinghong Y, et al. Does fusion contribute to the improvement of LV systolic function of heart failure patients when pacing the LV with varying AV delays? (abstract) Pacing Clin Electrophysiol 1999; 22:751, no copy available.

Auricchio A, Stellbrink C, Block M, et al. The effect of pacing chamber and atrio-ventricular delay on acute systolic function of paced patients with congestive heart failure. Circulation, 1999; 99: 2993-3001.

Auricchio A, Stellbrink C, Sack S, et al. The Pacing Therapies for Congestive Heart Failure (PATH-CHF) Study: Rationale, design, and endpoints of a prospective randomized multicenter study. Am J Cardiol 1999;83:Suppl 5B:130D-5D, Abstract only.

Badke FR, Boinay P, Covell JW. Effects of ventricular pacing on regional left ventricular performance in the dog. Heart Circ Physiol 1980: 7:H858-67, Abstract only.

Bailer, D., H.G. Wolpers, J. Zipfel, A. Hoeft, and G. Hillige. 1981. Unfavorable effects of ventricular pacing on myocardial energetics. *Basic Res Cardiol* 76:115-123, Abstract only.

Bailer, D., H.G. Wolpers, J. Zipfel, H.J. Bretschneider, and G. Hellige. 1988. Comparison of the effects of right atrial, right ventricular apex and atrioventricular sequential pacing on myocardial oxygen consumption and cardiac efficiency: a laboratory investigation. *Pacing Clin Electrophysiol* 11:394-403, Abstract only.

Blanc JJ, Etienne Y, Gilard M, et al. Evaluation of different ventricular pacing sites in patients with severe heart failure. Results of an acute hemodynamic study. Circulation 1997; 96: 3273-77.

Bristow MR, Feldman AM, Saxon LA. Heart failure management using implantable devices for ventricular resynchronization: Comparison of Medical Therapy, Pacing, and Defibrillation in Chronic Heart Failure (COMPANION) trial. COMPANION Steering Committee and COMPANION Clinical Investigators. J Card Fail Sep. 2000;6(3):276-85, Abstract only.

Burkhoff, D., R.Y. Oikawa, and K. Sagawa. 1986. Influence of pacing site on canine left ventricular contraction. *Am J Physiol* 251:H428-H435, Abstract only.

Cazeau S, Leclercq C, Lavergne T, et al. Effects of multisite biventricular pacing in patients with heart failure and intraventricular conduction delay. N Engl J Med Mar. 22, 2001;344(12):873-80.

Frais MA, Botvinick EH, Shosa DW, et al. Phase image characterization of ventricular contraction in left and right bundle branch block. Am J Cardiol 1982; 50:95-105, Abstract only.

Fried AG, Parker AB, Newton GE, Parker JD. Electrical and hemodynamic correlates of the maximal rate of pressure increase in the human left ventricle. J Card Fail 1999; 5:8-16, Abstract only.

Glikson M, Hayes DL, Nishimura RA. Newer clinical applications of pacing. J Cardiovasc Electrophysiol;8(10):1190-203, Abstract only, Oct. 8, 1997.

Grines CL, Bashore TM, Boudoulas H, et al. Functional abnormalities in isolated left bundle branch block. The effect of interventricular asynchrony. Circulation 1989; 79:845-53.

Kass DA, Chen CH, Curry C, et al. Improved left ventricular mechanics from acute VDD pacing in patients with dilated cardiomyopathy and ventricular conduction delay. Circulation 1999;99:1567-73.

Kerwin WF, Botvinick EH, O'Connell JW, et al. Ventricular contraction abnormalities in dilated cardiomyopathy: effect of biventricular pacing to correct interventricular dyssynchrony. J Am Coll Cardiol 2000; 35:1221-7.

Medtronic INSYNC® III, Device Model 8042, Device Reference Guide, 2006, pp. 1-231.

Medtronic INSYNC® III 8042, Atrial Synchronous Biventricular Pacing Device, Implant Manual, 2001, p. 1-21.

Miyazawa K, Arai T, Shirato K, Haneda T, Ikeda S. Regional contraction patterns of the left ventricle during ventricular pacing. J Exp Med 1977; 122:167-74, Abstract only.

Nelson GS, Berger RD, Fetics BJ, Talbot M, Hare JM, Kass DA, Spinelli JC. Left ventricular or biventricular pacing improves cardiac function at diminished energy cost in patients with dilated cardiomyopathy and left bundle-branch block. Circulation Dec. 19, 2000;102(25):3053-9.

Obias-Manno D. Unconventional applications in pacemaker therapy. AACN Clin Issues Feb. 2001;12(1):127-39.

Owen, C.H., D.J. Esposito, J.W. Davis, and D.D. Glower. 1998. The effects of ventricular pacing on left ventricular geometry, function, myocardial oxygen consumption, and efficiency of contraction in conscious dogs. *Pacing Clin Electrophysiol* 21:1417-1429, Abstract only.

Park RC, Little WC, O'Rourke. Effect of alteration of left ventricular activation sequence on the left ventricular end-systolic pressure-volume relation in closed-chest dogs. Circ Res 1985; 57:706-17.

Prinzen, F.W., W.C. Hunter, B.T. Wyman, and E.R. McVeigh. 1999. Mapping of regional myocardial strain and work during ventricular pacing: experimental study using magnetic resonance tagging. *J Am Coll Cardiol* 33:1735-1742.

Rosenqvist, M., L. Bergfeldt, Y. Haga, J. Ryden, L. Ryden, and A. Owall. 1996. The effect of ventricular activation sequence on cardiac performance during pacing. *Pacing Clin Electrophysiol* 19:1279-1286, Abstract only.

Rosenqvist, M., K. Isaac, E.H. Botvinick, M.W. Dae, J. Cockrell, J.A. Abbott, N.B. Schiller, and J.C. Griffin. 1991. Relative importance of activation sequence compared to atrioventricular synchrony in left ventricular function. *Am J Cardiol* 67:148-156, Abstract only.

Saxon LA, Kerwin WF, Cahalan MK, et al. Acute effects of intraoperative multisite ventricular pacing on left ventricular function and activation/contraction sequence in patients with depressed ventricular function. J Cardiovasc Electrophysiol 1998; 9: 13-21, Abstract only.

Shamim W, Francis DP, Yousufuddin M, et al. Intraventricular conduction delay: a prognostic marker in chronic heart failure. Int J Cardiol 1999; 70:171-8, Abstract only.

Xiao HB, Brecker SJ, Gibson DG. Effects of abnormal activation on the time course of the left ventricular pressure pulse in dilated cardiomyopathy. Br Heart J 1992; 68:403-7.

Xiao HB, Roy C, Fujimoto S, Gibson DG. Natural history of abnormal conduction and its relation to prognosis in patients with dilated cardiomyopathy. Int J Cardiol 1996; 53:163-70, Abstract only.

Office Action from U.S. Appl. No. 10/270,035 dated Feb. 17, 2006, 11 pages.

Office Action from U.S. Appl. No. 10/270,035 dated Jul. 27, 2006, 10 pages.

Notice of Allowance dated Feb. 20, 2007 from U.S. Appl. No. 10/270,035, 4 pages.

Office Action Response dated Dec. 1, 2006 from U.S. Appl. No. 10/270,035, 12 pages.

Office Action Response dated May 15, 2006 from U.S. Appl. No. 10/270,035, 12 pages.

(56) References Cited

OTHER PUBLICATIONS

Office Action Response dated Sep. 12, 2005 from U.S. Appl. No. 10/270,035, 9 pages.
Interview Summary dated Aug. 9, 2005 from U.S. Appl. No. 10/270,035, 4 pages.
Office Action dated Jul. 8, 2005 from U.S. Appl. No. 10/270,035, 7 pages.
Office Action Response dated Jun. 29, 2005 from U.S. Appl. No. 10/270,035, 7 pages.

\* cited by examiner

| Biventricular Pacing Code | | | LRL Timing Events | | | |
|---|---|---|---|---|---|---|
| Ventricles Paced | Ventricles Sensed | Ventricular Timing | RVP | LVP | RVS | LVS |
| B | B | R | X | | X | |
| B | B | L | | X | | X |
| B | B | B | X | X | X | X |
| B | R | R | X | | X | |
| B | R | L* | | X | | |
| B | R | B | X | X | X | |
| B | L | R* | X | | | |
| B | L | L | | X | | X |
| B | L | B | X | X | | X |
| R | B | R | X | | X | |
| R | B | L‡ | | | | X |
| R | B | B | X | | X | X |
| R | R | R | X | | X | |
| R | R | L* | | | | |
| R | R | B+ | X | | X | |
| R | L | R* | X | | | |
| R | L | L | | | | X |
| R | L | B | X | | | X |
| L | B | R‡ | | | X | |
| L | B | L | | X | | X |
| L | B | B | | X | X | X |
| L | R | R | | | X | |
| L | R | L* | | X | | |
| L | R | B | | X | X | |
| L | L | R+ | | | | |
| L | L | L | | X | | X |
| L | L | B+ | | X | | X |

\* indicates timing using a channel in which sensing is absent
\+ indicates timing using a channel in which pacing or sensing is absent
‡ indicates timing using a channel in which pacing is absent

Figure 9

TIMING CYCLES FOR SYNCHRONIZED MULTISITE CARDIAC PACING

RELATED APPLICATIONS

This application is a division of U.S. patent application Ser. No. 10/270,035 filed on Oct. 11, 2002, to issue as U.S. Pat. No. 7,260,432 on Aug. 21, 2007, which claims the benefit of Provisional Patent Application Ser. No. 60/328,872, filed on Oct. 11, 2001, to which Applicant claims priority under 35 U.S.C. §120 and 35 U.S.C. §119(e), respectively, and which are incorporated herein by reference.

FIELD OF THE INVENTION

The present invention relates generally to medical devices and, more particularly, to identifying groups of cardiac events associated with depolarization wavefronts. Furthermore, the present invention relates to using identified groups of cardiac events associated with depolarization wavefronts to coordinate the delivery of pacing therapy to the heart.

BACKGROUND OF THE INVENTION

Rhythmic contractions of a healthy heart are normally controlled by the sinoatrial (SA) node which includes specialized cells located in the superior right atrium. The SA node is the normal pacemaker of the heart, typically initiating 60-100 heart beats per minute. When the SA node is pacing the heart normally, the heart is said to be in normal sinus rhythm (NSR).

The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management devices have been developed that provide pacing stimulation to one or more heart chambers in an attempt to improve the rhythm and coordination of atrial and/or ventricular contractions. Cardiac rhythm management devices may incorporate defibrillation and/or pacemaker circuitry used to treat patients with serious arrhythmias. Cardiac rhythm management devices typically include circuitry to sense signals from the heart and a pulse generator for providing electrical stimulation to the heart. Leads extending into the patient's heart are coupled to electrodes that contact the myocardium for sensing the heart's electrical signals and for delivering stimulation to the heart in accordance with various therapies for treating cardiac arrhythmias. Cardiac rhythm management devices may deliver low energy electrical pace pulses timed to assist the heart in producing a contractile rhythm that maintains cardiac pumping efficiency appropriate to meet the metabolic requirements of the patient.

SUMMARY OF THE INVENTION

For the reasons stated above, and for other reasons stated below which will become apparent to those skilled in the art upon reading the present specification, there is a need in the art for an approach for multisite cardiac sensing and pacing. The invention has been found to be particularly useful in identifying groups of cardiac events associated with a depolarization wavefront and using one or more cardiac events of the groups to establish timing cycles for synchronized multisite pacing therapy.

In one embodiment of the invention, a method involves detecting cardiac events associated with a number of cardiac sites in a single heart chamber or in bilateral heart chambers. A group of the detected cardiac events associated with a depolarization wavefront representing a myocardial activation initiated at a particular cardiac site and conducted to other cardiac sites is identified.

Another embodiment of the invention involves detecting events in a left and a right atrium. A pair of detected cardiac events associated with a depolarization wavefront is identified.

In yet another embodiment of the invention, a medical device includes a lead system having electrodes for detecting cardiac events at a number of cardiac sites in a single heart chamber or bilateral heart chambers. The device also includes sensing circuitry coupled to the lead system and configured to sense cardiac signals transmitted through the lead electrodes. A control system is arranged to detect cardiac events associated with the plurality of cardiac sites and identify a group of the detected cardiac events associated with a depolarization wavefront.

In accordance with a further embodiment of the invention, a system includes means for detecting cardiac events associated with a plurality of cardiac sites in a single heart chamber or in bilateral heart chambers and means for identifying a group of the detected cardiac events associated with a depolarization wavefront.

In accordance with yet another embodiment of the invention, a system includes means for detecting right ventricular cardiac events associated with a right ventricular cardiac site, means for detecting left ventricular cardiac events associated with a left ventricular cardiac site, and means for identifying a pair of the detected cardiac events associated with a depolarization wavefront, the depolarization wavefront representing a myocardial activation initiated at one of the cardiac sites and conducted to the other cardiac site.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 9 is a table specifying synchronized multisite pacing modes with a letter code in accordance with an embodiment of the invention;

Figure 1A:
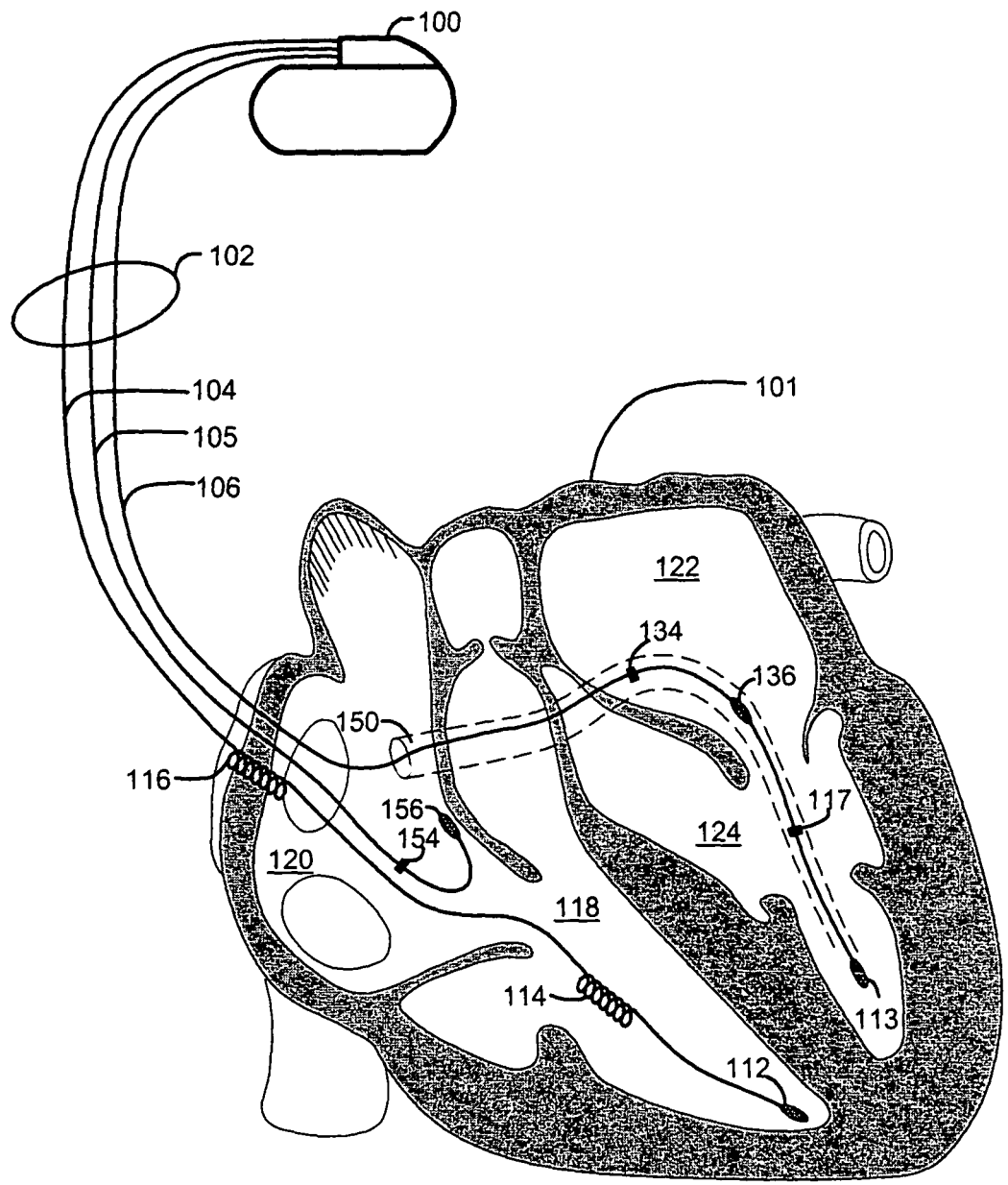
FIGS. 1A and 1B are partial views of embodiments of an implantable medical device with an endocardial lead system extending into the heart and the cardiac venous system with electrodes positioned at multiple locations in or adjacent to various heart chambers.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Over the past several decades, pacing has become an important therapy for patients with various forms of bradycardia, including in particular, AV conduction delay and sinus node dysfunction. Atrioventricular pacing was introduced as a method of better meeting the metabolic needs of many patients with sinus node and atrioventricular conduction abnormalities. Atrioventricular pacing involves sensing or pacing an atrium and a ventricle, typically the right atrium and the right ventricle. Pacing bilateral heart chambers, e.g., the left and right atria or the left and right ventricle, simultaneously or in phased sequence can enhance coordination of the bilateral chambers, thereby increasing the heart's pumping action. Furthermore, pacing at two or more sites within a particular heart chamber may also enhance hemodynamic efficiency.

Heart failure is often associated with prolonged ventricular conduction delay, such as left bundle branch block, which contributes to left ventricular systolic dysfunction and poor outcome. Ventricular conduction delay generates uncoordinated ventricular contractions that reduce pumping effectiveness. Studies of heart failure patients in normal sinus rhythm with left ventricular conduction delay indicate that atrio-biventricular pacing can improve systolic function and energetics. Biventricular pacing may resynchronize right and left ventricular contractions as well as left ventricular septal and lateral wall contractions.

Another application of biventricular pacing is to correct the left ventricular contraction delay induced by pacing only the right ventricle which reduces contractile function, cardiac output, and cardiac metabolic efficiency. When cardiac function is already depressed by heart disease, such as dilated cardiomyopathy or atrial fibrillation, further decline in heart function from right ventricular pacing may not be tolerated and may contribute to worsening symptoms and failure progression.

Devices capable of multichamber or multisite pacing may be used to treat contractile dysfunction, while concurrently treating bradycardia and tachycardia. Such devices, denoted cardiac function management devices, or CFM devices, are configured to improve pumping function by altering heart chamber contraction sequences while maintaining pumping rate and rhythm.

A cardiac rhythm management device incorporating a multichamber pacemaker may include electrodes positioned to contact cardiac tissue within or adjacent to both the left and the right ventricles for pacing both the left and right ventricles. Furthermore, a pacemaker may include electrodes positioned to contact tissue within or adjacent to both the left and the right atria to enable bi-atrial pacing. Bi-atrial or bi-ventricular pacing may be used to improve the coordination of cardiac contractions between the bilateral heart chambers. Furthermore, cardiac rhythm management device incorporating a multisite pacemaker may include leads positioned in or adjacent to a heart chamber and positioned appropriately to pace two sites of the heart chamber.

Embodiments of the present system illustrated herein are generally described as being implemented in a cardiac function management (CFM) device incorporating a pacemaker that may operate in numerous pacing modes. In one embodiment, a CFM device configured as a multichamber defibrillator and pacemaker operates to stimulate the heart by delivering pace pulses according to various multichamber or multisite pacing timing modes. Many types of multiple chamber pacemaker/defibrillator devices may be used to implement the multichamber pacing modes of the present invention. Although the present system is described in conjunction with a CFM device having a microprocessor-based architecture, it will be understood that the CFM device may be implemented in any logic-based architecture, if desired. It is further understood that techniques of the present invention may be implemented in a variety of implantable or external devices, including CFM devices or other multichamber or multisite cardiac pacing or monitoring devices.

Referring now to FIG. 1A of the drawings, there is shown one embodiment of a medical device system which includes a CFM device 100 electrically and physically coupled to an intracardiac lead system 102. The intracardiac lead system 102 is implanted in a human body with portions of the intracardiac lead system 102 inserted into a heart 101. The intracardiac lead system 102 is used to detect and analyze electric cardiac signals produced by the heart 101 and to provide electrical energy to the heart 101 under certain predetermined conditions to treat cardiac arrhythmias.

The intracardiac lead system 102 includes one or more electrodes used for pacing, sensing, or defibrillation. In the particular embodiment shown in FIG. 1A, the intracardiac lead system 102 includes a right ventricular lead system 104, a right atrial lead system 105, and a left atrial/ventricular lead system 106. In one embodiment, the right ventricular lead system 104 is configured as an integrated bipolar pace/shock lead.

The right ventricular lead system 104 includes an SVC-coil 116, an RV-coil 114, and an RV-tip electrode 112. The RV-coil 114, which may alternatively be configured as an RV-ring electrode, is spaced apart from the RV-tip electrode 112, which is a pacing electrode for the right ventricle.

The right atrial lead system 105 includes a RA-tip electrode 156 and an RA-ring electrode 154. The RA-tip 156 and RA-ring 154 electrodes may provide respectively pacing pulses to the right atrium of the heart and detect cardiac signals from the right atrium. In one configuration, the right atrial lead system 105 is configured as a J-lead.

In this configuration, the intracardiac lead system 102 is shown positioned within the heart 101, with the right ventricular lead system 104 extending through the right atrium 120 and into the right ventricle 118. In particular, the RV-tip electrode 112 and RV-coil electrode 114 are positioned at appropriate locations within the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 1A are defibrillation electrodes.

An LV-tip electrode 113, and an LV-ring electrode 117 are inserted through the coronary venous system and positioned adjacent to the left ventricle 124 of the heart 101. The LV-ring electrode 117 is spaced apart from the LV-tip electrode, 113 which is a pacing electrode for the left ventricle. Both the LV-tip 113 and LV-ring 117 electrodes may also be used for sensing the left ventricle providing two sensing sites within the left ventricle. The left atrial/left ventricular lead system 106 further includes an LA-tip 136 and LA-ring 134 electrode positioned adjacent the left atrium 122 for pacing and sensing the left atrium 122 of the heart 101.

The left atrial/left ventricular lead system 106 includes endocardial pacing leads that are advanced through the superior vena cava (SVC), the right atrium 120, the valve of the coronary sinus, and the coronary sinus 150 to locate the LA-tip 136, LA-ring 134, LV-tip 113 and LV-ring 117 electrodes at appropriate locations adjacent to the left atrium and ventricle 122, 124, respectively. In one example, left atrial/ventricular lead placement involves creating an opening in a percutaneous access vessel, such as the left subclavian or left cephalic vein. The left atrial/left ventricular lead 106 is guided into the right atrium 120 of the heart via the superior vena cava.

From the right atrium 120, the left atrial/left ventricular lead system 106 is deployed into the coronary sinus ostium, the opening of the coronary sinus 150. The lead system 106 is guided through the coronary sinus 150 to a coronary vein of the left ventricle 124. This vein is used as an access pathway for leads to reach the surfaces of the left atrium 122 and the left ventricle 124 which are not directly accessible from the right side of the heart. Lead placement for the left atrial/left ventricular lead system 106 may be achieved via the subclavian vein access and a preformed guiding catheter for insertion of the LV and LA electrodes 113, 117, 136, 134 adjacent the left ventricle 124 and left atrium 122, respectively. In one configuration, the left atrial/left ventricular lead system 106 is implemented as a single-pass lead.

Figure 1B:
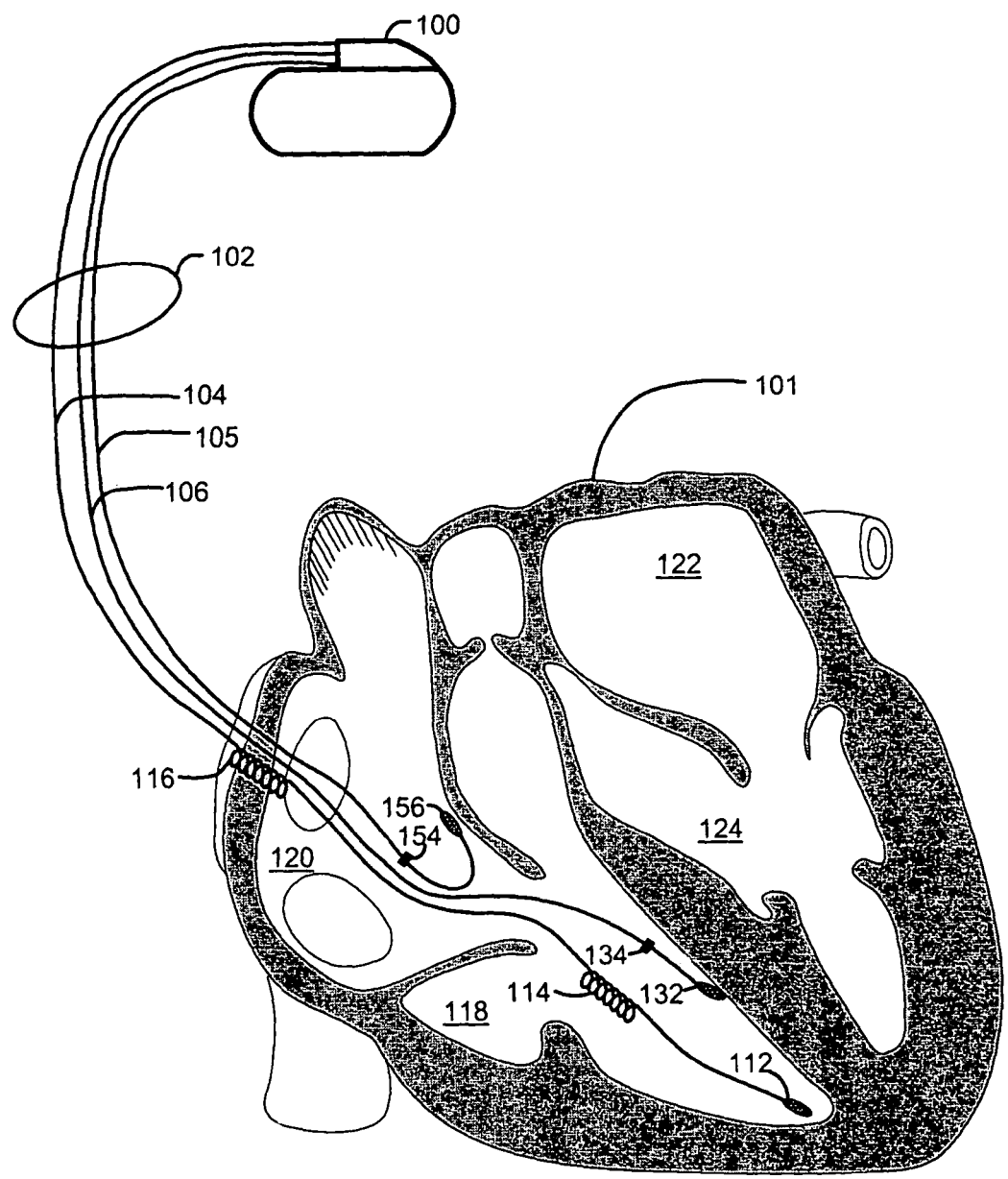

FIG. 1B shows one embodiment of a medical device system that may be used for synchronized multisite sensing or pacing within a heart chamber. The medical device system includes a CFM device 100 electrically and physically coupled to an intracardiac lead system 102. The intracardiac lead system 102 is implanted in a human body with portions of the intracardiac lead system 102 inserted into a heart 101. The intracardiac lead system 102 is used to detect and analyze electric cardiac signals produced by the heart 101 and to provide electrical energy to the heart 101 under certain predetermined conditions to treat cardiac arrhythmias.

The intracardiac lead system 102 includes one or more electrodes used for pacing, sensing, or defibrillation. In the particular embodiment shown in FIG. 1A, the intracardiac lead system 102 includes first and second right ventricular lead systems 104, 106 and a right atrial lead system 105. In one embodiment, the right ventricular lead system 104 is configured as an integrated bipolar pace/shock lead.

The first right ventricular lead system 104 includes an SVC-coil 116, an RV-coil 114, and an RV-tip electrode 112. The RV-coil 114, which may alternatively be configured as an RV-ring electrode, is spaced apart from the RV-tip electrode 112, which is a pacing electrode for the right ventricle. The first right ventricular lead system includes endocardial pacing leads that are advanced through the superior vena cava (SVC), the right atrium 120 and into the right ventricle 118 to contact myocardial tissue at a first pacing site within the right ventricle 118.

The second right ventricular lead system 106 includes an RV-tip electrode 132 and an RV-ring electrode 134. The first right ventricular lead system includes endocardial pacing leads that are advanced through the superior vena cava (SVC), the right atrium 120 and into the right ventricle 118 to contact myocardial tissue at a second pacing site within the right ventricle 118.

The right atrial lead system 105 includes a RA-tip electrode 156 and an RA-ring electrode 154. The RA-tip 156 and RA-ring 154 electrodes may provide respectively pacing pulses to the right atrium of the heart and detect cardiac signals from the right atrium. In one configuration, the right atrial lead system 105 is configured as a J-lead.

In this configuration, the intracardiac lead system 102 is shown positioned within the heart 101, with the first and the second right ventricular lead systems 104, 106 extending through the right atrium 120 and into the right ventricle 118. In particular, the RV-tip electrode 112 and RV-coil electrode 114 are positioned at appropriate locations to sense and pace a first site within the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 1B are defibrillation electrodes. An RV-tip electrode 132, and an RV-ring electrode 138 are positioned at appropriate locations to sense and pace a second site within the right ventricle 118.

Figure 2:
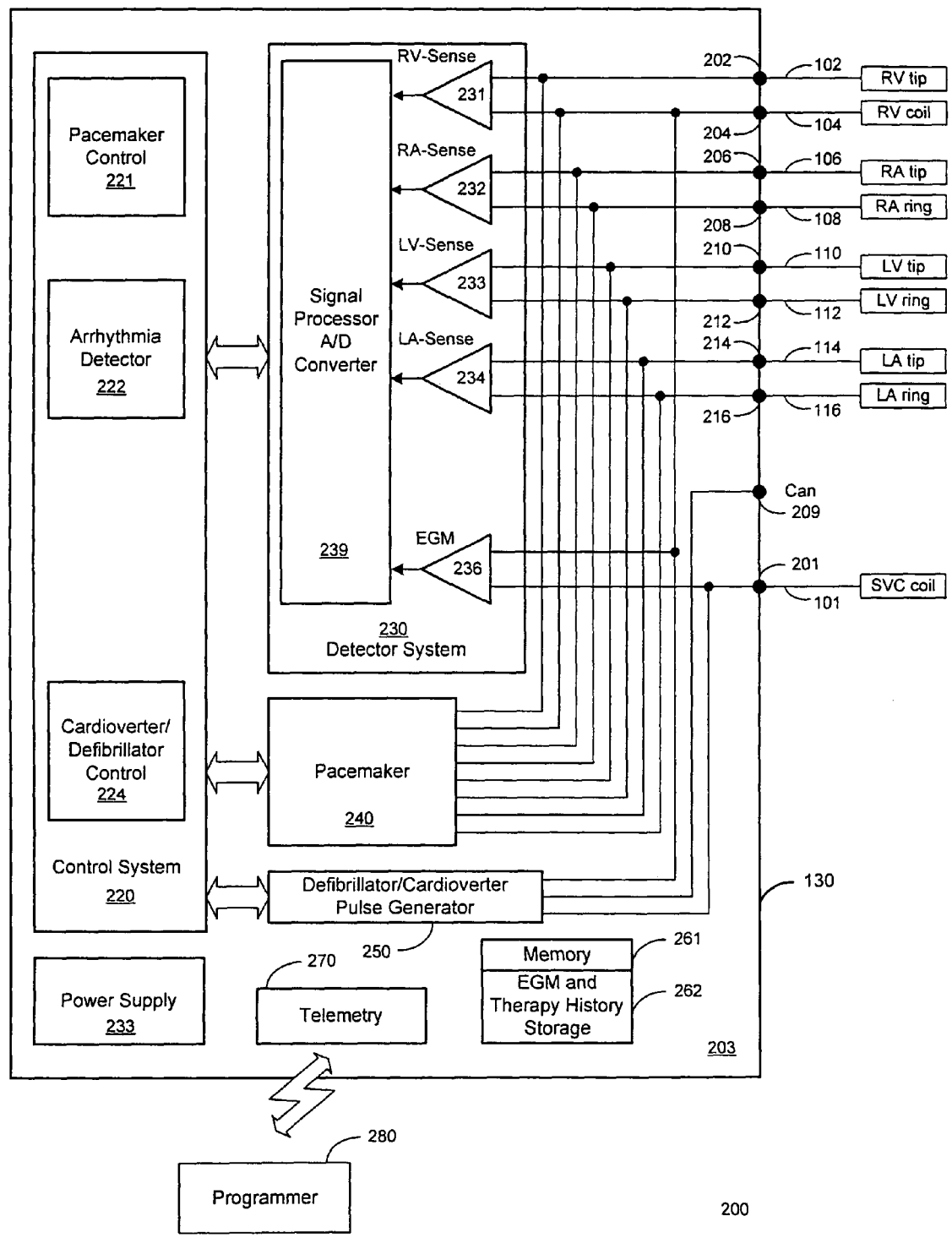
FIG. 2 is a system block diagram of an implantable medical device configured for multichamber cardiac sensing and pacing in accordance with an embodiment of the invention.

Referring now to FIG. 2, there is shown an embodiment of a CFM device 200 suitable for implementing timing cycles for synchronized pacing in accordance with various embodiments of the present invention. FIG. 2 shows a CFM device divided into functional blocks. There exist many possible configurations in which these functional blocks can be arranged. The example depicted in FIG. 2 is one possible functional arrangement. The CFM device 200 includes circuitry for receiving cardiac signals from a heart 101 (not shown in FIG. 2) and delivering electrical energy in the form of pace pulses or cardioversion/defibrillation pulses to the heart.

The right ventricular lead system includes conductors 182 and 184 for transmitting sense and pacing signals between terminals 202 and 204 of the CFM device and the RV-tip and RV-coil electrodes, respectively. The right ventricular lead system further includes conductor 181 for transmitting signals between the SVC coil and terminal 201 of the CFM device 200. The right atrial lead system includes conductor 186 for transmitting signals between the RA-tip electrode and terminal 206 and conductor 188 for transmitting signals between the RA-ring electrode and terminal 208.

The left atrial/ventricular lead system includes conductors 190, 192 for transmitting sense and pacing signals between terminals 210, 212 of the CFM device 200 and LV-tip and LV-ring electrodes respectively. The left atrial/ventricular lead system also includes LA-tip and LA ring electrodes. A can electrode 209 coupled to a housing 130 of the CFM device 200 is also provided.

In one embodiment, the CFM device circuitry 203 is encased in a hermetically sealed housing 130 suitable for implanting in a human body. Power to the CFM device 200 is supplied by an electrochemical battery 233 that is housed within the CFM device 200. In one embodiment, the CFM circuitry 203 is a programmable microprocessor-based system, including a control system 220, detector system 230, pacemaker 240, cardioverter/defibrillator pulse generator 250 and a memory circuit 261. The memory circuit 261 stores parameters for various pacing, defibrillation, and sensing modes and stores data indicative of cardiac signals received by other components of the CFM circuitry 203. A memory is also provided for storing historical EGM and therapy data 262, which may be used on-board for various purposes and transmitted to an external programmer unit 280 as required.

The control system 220 may use various control subsystems including pacemaker control 221, cardioverter/defibrillator control 224, and arrhythmia detector 222. The control system 220 may encompass additional functional components (not shown) for controlling the CFM circuitry 203. The control system 220 and memory circuit 261 cooperate with other components of the CFM circuitry 203 to perform operations involving synchronized pacing according to the principles of the present invention, in addition to other sensing, pacing and defibrillation functions.

Telemetry circuitry 270 is additionally coupled to the CFM circuitry 203 to allow the CFM device 200 to communicate with an external programmer unit 280. In one embodiment, the telemetry circuitry 270 and the programmer unit 280 use a wire loop antenna and a radio frequency telemetric link to receive and transmit signals and data between the programmer unit 280 telemetry circuitry 270. In this manner, programming commands may be transferred to the CFM circuitry 203 from the programmer unit 280 during and after implant. In addition, stored cardiac data relevant to synchronized pacing therapy, along with other data, may be transferred to the programmer unit 280 from the CFM device 200, for example.

Cardiac signals sensed through use of the RV-tip and LV-tip electrodes are near-field signals as are known in the art. More particularly, a signal derived from the right ventricle is detected as a voltage developed between the RV-tip electrode and the RV-coil. RV-tip and RV-coil electrodes are shown coupled to an RV-sense amplifier 231 located within the detector system 230. Signals received by the RV-sense amplifier 231 are communicated to the signal processor and A/D converter 239. The RV-sense amplifier 231 serves to sense and amplify the signals. The signal processor and A/D converter 239 convert the R-wave signals from analog to digital form and communicate the signals to the control system 220.

Signals derived from the left ventricle are detected as a voltage developed between the LV-tip electrode and the LV-ring electrode. LV-tip and LV-ring electrodes are shown coupled to an LV-sense amplifier 233 located within the detector system 230. Signals received by the 233 are communicated to the signal processor and A/D converter 239. The LV-sense amplifier 233 serves to sense and amplify the signals. The signal processor and A/D converter 239 convert the R-wave signals from analog to digital form and communicate the signals to the control system 220.

Cardiac signals sensed through use of one or both of the RV-coil and the SVC-coil are far-field signals, also referred to as morphology or shock channel signals, as are known in the art. More particularly, a shock channel signal is detected as a voltage developed between the RV-coil and the SVC-coil. A shock channel signal may also be detected as a voltage developed between the RV-coil and the SVC-coil coupled to the can electrode 209. Shock channel signals developed using appropriate combinations of the RV-coil, SVC-coil, and can electrode are sensed and amplified by a shock EGM amplifier 236 located in the detector system 230. The output of the EGM amplifier 236 is coupled to the control system 220 via the signal processor and A/D converter 239.

RA-tip and RA-ring electrodes are shown coupled to an RA-sense amplifier 232 located within the detector system 230. Atrial sense signals received by the RA-sense amplifier 232 in the detector system 230 are communicated to an A/D converter 239. The RA-sense amplifier serves to sense and amplify the A-wave signals of the right atrium. The A/D converter 239 converts the sensed signals from analog to digital form and communicates the signals to the control system 220.

A-wave signals originating in the left atrium are sensed by the LA-tip and LA-ring electrodes. The A-waves are sensed and amplified by the LA-sense amplifier 234 located in the detector system. The LA-sense amplifier serves to sense and amplify the A-wave signals of the left atrium. The A/D converter 239 converts the sensed signals from analog to digital form and communicates the signals to the control system 220.

The pacemaker 240 communicates pacing signals to the pacing electrodes, RV-tip, RA-tip, LV-tip and LA-tip, according to a pre-established pacing regimen under appropriate conditions. Blanking circuitry (not shown) is employed in a known manner when ventricular or atrial pacing pulses are delivered, such that the ventricular channels, atrial channels, and shock channel are properly blanked at the appropriate time and for the appropriate duration.

Figure 3:
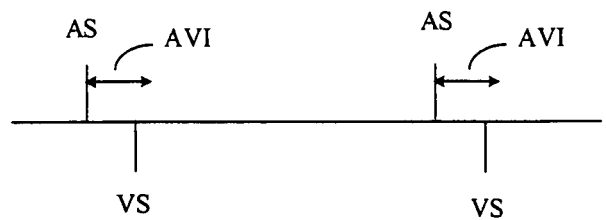
FIG. 3 is a timing diagram illustrating intact AV conduction and adequate ventricular rates.

CFM devices may be adapted to improve pumping function by altering contraction sequences in a manner distinct from conventional bradycardia pacing. To treat bradycardia, pacing may be performed when the heart rate is not fast enough or the atrioventricular (AV) interval is too long. Thus, as shown in the pacing diagram of FIG. 3, patients with intact AV conduction and adequate ventricular rates may not be paced at all if, following a sensed intrinsic atrial event, AS, AV conduction occurs before the programmed AV interval has elapsed and an intrinsic ventricular event, VS, is sensed.

Figure 4:
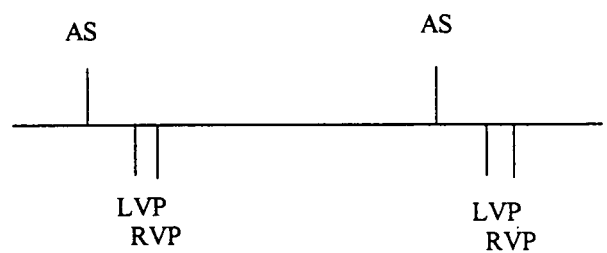
FIG. 4 is a timing diagram illustrating a pacing mode involving pacing both the left ventricle and the right ventricle after a sensed atrial contraction in accordance with an embodiment of the invention.

To improve pumping function, two or more heart chambers may be paced simultaneously or in phased sequence, thus coordinating inefficient or non-existent contraction sequences. For example, FIG. 4 illustrates a pacing mode involving pacing both the left ventricle, LVP, and the right ventricle, RVP, after a sensed atrial contraction, AS. Such a pacing mode may mitigate pathological ventricular conduction delays, thereby improving the pumping function of the heart.

In general, embodiments of the present invention indicate various pacing timing cycle rules for multichamber pacing or multisite pacing in CFM devices. In multichamber pacing, there may be a programmed or intrinsic difference in the timing of events in bilateral heart chambers. In addition, pacing of the bilateral chambers may be synchronized with normal sinus rhythm. Although the present invention is generally described in terms of timing cycles for biventricular pacing, it is understood that the timing cycle rules described herein may also be applied to any type of multisite pacing, including bi-atrial pacing or pacing at multiple sites within one heart chamber, for example.

At the lower rate and at atrial rates up to the maximum tracking rate, synchronized biventricular pacing may be used to coordinate left and right ventricular and intraventricular regional wall contractions. Such biventricular pacing may also be synchronized with normal sinus rhythm sensed in the right atrium. In biventricular pacing, there may be a programmed or intrinsic difference in the timing of the left and right ventricular events that lead to several variations of the AV interval. Embodiments of the present invention describe various pacing timing modes that may be used for heart rate timing and initiating pacing intervals in multisite pacing.

In multichamber pacing, timing from events in either chamber may be combined in a variety of ways to control heart rate. For example, in biventricular pacing, the first occurring ventricular sense, whether right or left, could reset the VA escape interval (VAI) and cardiac cycles may then be based on intervals between the first ventricular sensed events in each cycle. However, heart rate intervals may vary because they may be started and stopped by events in opposite heart chambers.

Figure 5:
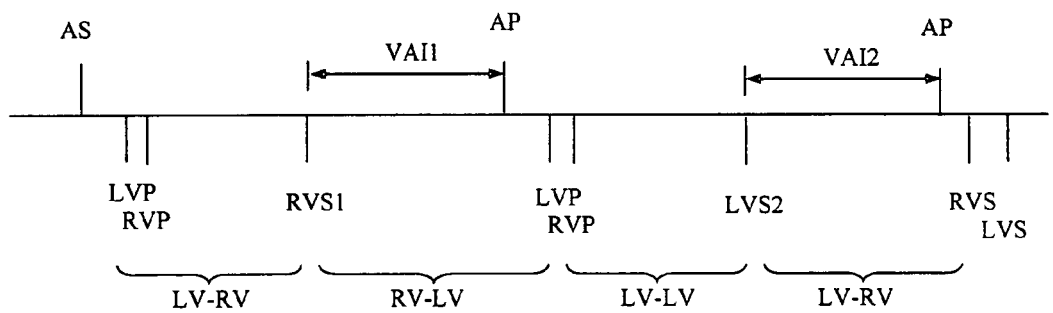
FIG. 5 is a timing diagram illustrating representative pacing timing cycles in accordance with embodiments of the invention.

Examples of representative pacing timing cycles in accordance with embodiments of the invention are illustrated in FIG. 5. For example, pacing escape intervals may be initiated by a first sensed or paced ventricular event in each cycle. A first ventricular event, whether from the right ventricle or the left ventricle, may be used to reset the VA escape interval (VAI). As illustrated in FIG. 5, a first ventricular sense from the right ventricle RVS1 resets the VA interval VAI1, and a first ventricular sense from the left ventricle LVS2 resets the VA interval VAI2.

Figure 6:
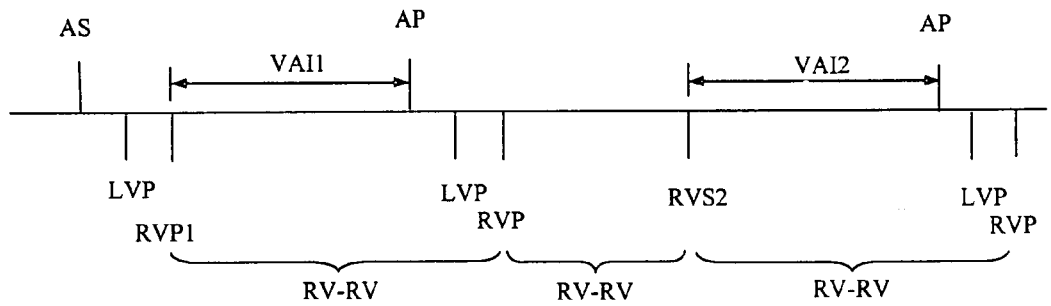
FIG. 6 is a timing diagram illustrating RV based timing in accordance with embodiments of the invention.

Alternatively, left ventricular or right ventricular events only may be used to control heart rate, resulting in LV based timing or RV based timing. For example, in RV based timing, as illustrated in FIG. 6, a right ventricular pace RVP1 or sense RVS2 may reset the VA interval VAI1, VAI2. Thus, in this example, heart rate is derived from intervals based on right ventricular events only.

Timing associated with multichamber pacing may be further complicated by the possibility of a delay between pacing pulses delivered to the chambers. For example, a delay between right and left ventricular pacing may allow multiple definitions of AV and VA escape intervals. With a conventional atrioventricular device, the pacing rate may be defined as the sum of the VA and AV escape intervals. In a multichamber device, such as one used for synchronized biventricular pacing, the VA and AV escape intervals may be based on events occurring in a particular ventricle or a first occurring event in either ventricle. When both ventricles are paced, the pacing delay between the right and left ventricles may be denoted the RV-LV interval.

Figure 7A:
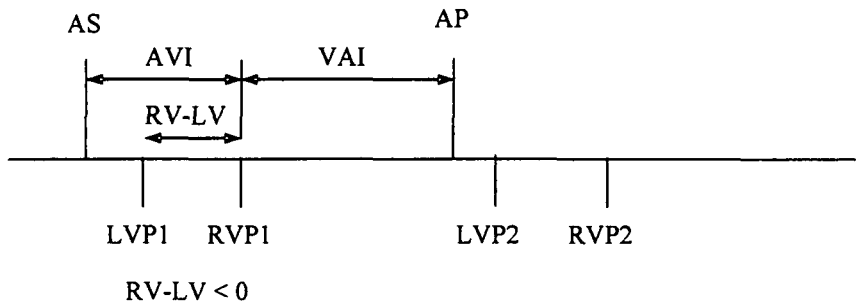
FIGS. 7A-7C illustrate examples of various configurations of the RV-LV interval in accordance with embodiments of the invention.
Figure 7B:
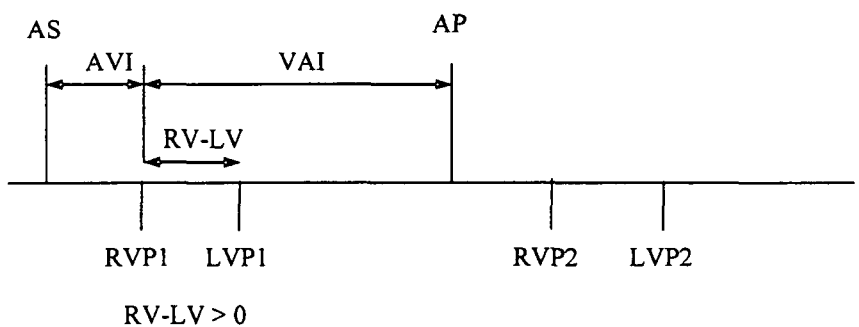
Figure 7C:
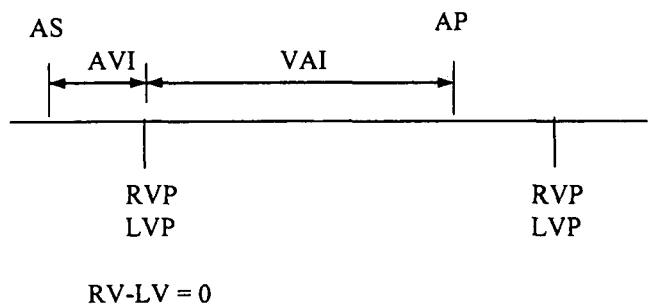

FIGS. 7A-7C illustrate examples of various configurations of the RV-LV interval. The RV-LV interval may be characterized by a negative time interval when the left ventricle is paced first and the right ventricle is paced second, as illustrated in FIG. 7A. In this situation, the left ventricle is paced LVP1 within the AV escape interval AVI and the VA escape interval VAI begins with the right ventricle pace RVP1. In another example, illustrated in FIG. 7B, the RV-LV interval may be characterized by a positive time interval when the right ventricle is paced before the left ventricle. In this situation, the right ventricular pace RVP1 initiates the VA interval VAI and occurs upon the expiration of the AV interval AVI. The left ventricular pace LVP1 occurs within the VA interval VAI. In yet another example, illustrated in FIG. 7C, the right ventricle and the left ventricle RVP, LVP are paced simultaneously at the expiration of the AV interval AVI, initiating the VA interval VAI and producing an RV-LV time interval of zero.

Figure 8:
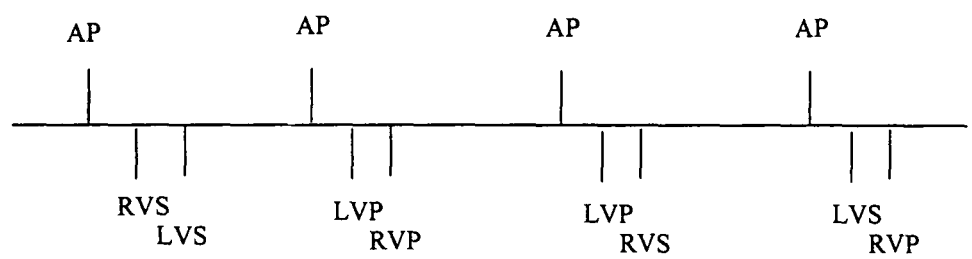
FIG. 8 illustrates various combinations of right ventricular and left ventricular paced and sensed events that may occur following an atrial pace in accordance with an embodiment of the invention.

At lower pacing rates, atrial pacing will occur as in atrioventricular timing. The atrial paced events are followed by various combinations of LV and RV paced or sensed events. FIG. 8 illustrates various combinations of right ventricular and left ventricular paced and sensed events that may occur following an atrial pace. Thus, the events initiating the atrial escape interval VAI may depend on the combination of ventricular pacing, sensing, and ventricular timing.

It is possible to specify synchronized multisite pacing modes with a three letter code as described in FIG. 9. The codes specified in FIG. 9 are analogous to the bradycardia pacing code in standard use for dual chamber pacemakers. For example, the first letter of a biventricular pacing code would specify whether the right (R), left (L), or both (B) ventricular chambers are paced. The second letter would specify which ventricular chambers are sensed, that is R, L, or B. The third letter would specify which ventricular chambers are used to reset the cardiac timing cycle, that is R, L, or B. In addition the letter T may also be used to indicate biventricular triggered modes. The synchronized biventricular pacing code may be combined with the standard bradycardia pacing code, for example, to describe the behavior of a CFM device with biventricular pacing.

In atrioventricular timing cycles, the maximum tracking rate (MTR) limit determines the maximum atrial interval tracked by the CFM. Upper rate behavior in atrioventricular timing cycles is characterized by pseudo-Wenckebach and repetitive intervals of prolonged P-V intervals. These prolonged P-V intervals can diminish the effectiveness of biventricular pacing by compromising ventricular filling patterns. Furthermore, with intact AV conduction, atrial rates exceeding the MTR may result in continuous AV conducted ventricular sensing that inhibits biventricular pacing. In most patients with heart failure, exercise is the period when it is most necessary to preserve 1:1 atrial-synchronous biventricular pacing. Therefore, in general, the MTR should exceed the patient's maximum physiological sinus rate. Biventricular pacing can then be preserved event at peak exercise.

Figure 10A:
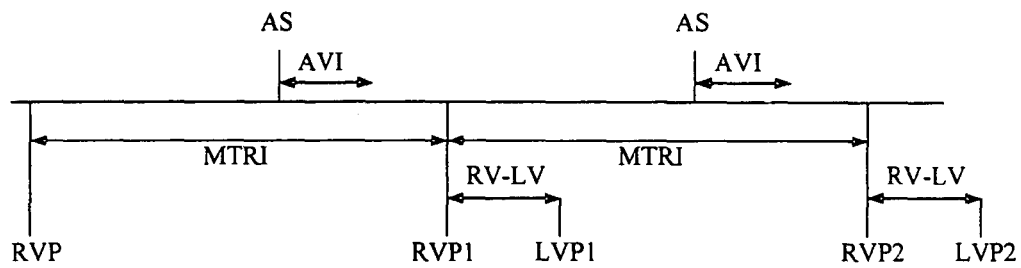
FIGS. 10A and 10B illustrate enforcement of a maximum tracking rate in accordance with an embodiment of the invention.
Figure 10B:
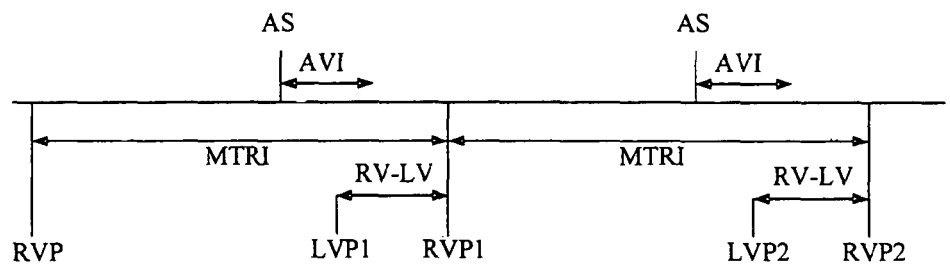

In atrioventricular timing, the maximum tracking rate is enforced by delaying the ventricular pace to the MTR interval when the AV interval expires during the MTR interval. When biventricular pacing includes a positive or negative RV-LV interval, pacing at the maximum tracking rate is adjusted according to the timing mode. For example, as illustrated in FIG. 10A, with RV-based timing and positive RV-LV interval, the right ventricular pace RVP1, RVP2 occurs at the end of the MTR followed after the RV-LV interval by the left ventricular pace LVP1, LVP2. With a negative RV-LV interval, the right ventricular pace RVP1, RVP2 still occurs at the end of the MTR interval, but is preceded by the left ventricular pace LVP1, LVP2 at the beginning of the RV-LV interval, as illustrated in FIG. 10B.

Biventricular pacing may be combined with right ventricle only sensing, left ventricle only sensing, or biventricular sensing to control how sensed events reset pacing intervals. As with atrioventricular pacing, intrinsic events sensed in a ventricular chamber may inhibit pacing in that chamber to avoid asynchronous pacing during a vulnerable period that might initiate tachycardia. With biventricular sensing, sensed events in the right and left ventricles will inhibit right and left ventricular paces, respectively, as illustrated in FIG. 11.

Figure 11:
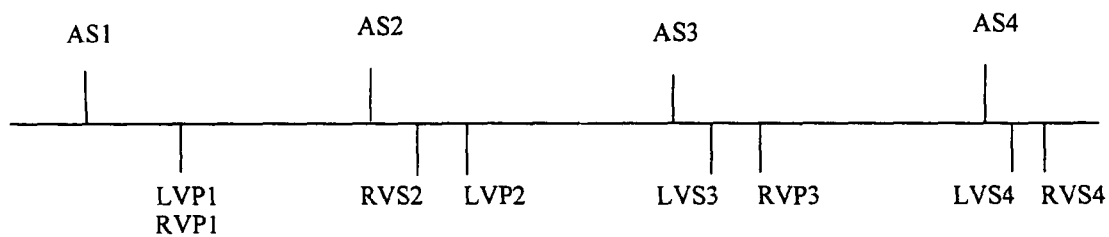
FIG. 11 is a timing diagram illustrating inhibition of right and left ventricular paces by sensed events in the right and left ventricles in accordance with an embodiment of the invention.

In FIG. 11, both the left and the right ventricle may be paced if no intrinsic events are sensed in either chamber. Thus a left ventricular pace LVP1 and a right ventricular pace RVP1 are delivered following a sensed atrial event AS1. The pacing may be delivered simultaneously to both ventricles, or in phased sequence according to a positive or negative RV-LV interval, for example.

A sensed event in the right ventricle RVS2 may inhibit a right ventricular pace, with the left ventricle pace LVP2 occurring according to the programmed RV-LV interval or other delay interval. A sensed event in the left ventricle LVS3 may inhibit the left ventricle pace and the right ventricle may be paced RVP3 according to a delay interval. Finally, sensed events in both chambers LVS4, RVS4 may inhibit both left ventricular and right ventricular paces.

Figure 12:
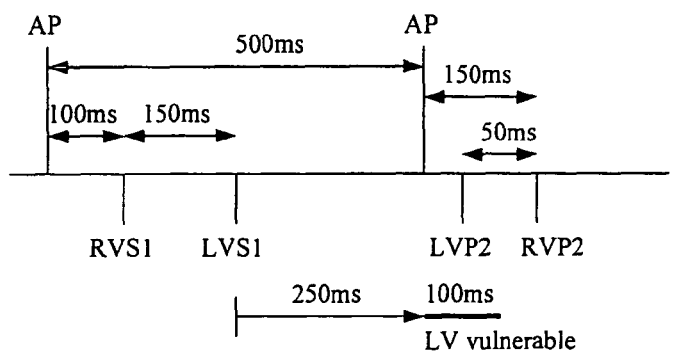
FIG. 12 is a timing diagram illustrating competitive pacing during a vulnerable period.

In biventricular pacing, prolonged RV-LV intervals present a risk of competitive pacing. Whenever a ventricular depolarization is not sensed, there is a risk of pacing that ventricle when it is no longer refractory, potentially stimulating a ventricular arrhythmia. The likelihood of competitive pacing may be increased by combinations of several factors, including prolonged right to left conduction delays typical of patients for whom biventricular pacing is currently indicated, long RV-LV pacing intervals that have opposite signs from intrinsic RV-LV intervals, fast pacing rates, and sensed ventricular cross-chamber refractory periods. For example, as illustrated in FIG. 12, if the intrinsic RV-LV conduction interval is 150 ms, pacing at an interval of 500 ms with a negative RV-LV delay of 50 ms may increase the risk of competitive pacing. In this example, the left ventricular paced event LVP2 may occur when the left ventricle is no longer refractory. In FIG. 12, as with other examples provided herein, RV based timing is used, although timing intervals based on LV based timing, first-in timing or any other timing for bi-chamber pacing may be used.

In one approach, the risk of competitive pacing may be minimized through the use of biventricular triggered pacing. Biventricular triggered pacing may prevent the long intrinsic RV-LV conduction delays, reducing the chance that a chamber will be subjected to pacing during the vulnerable period. Thus, whenever a right ventricular sense occurs, the left ventricle may be paced immediately and when a left ventricular sense occurs, the right ventricle is paced immediately. This strategy is most effective if it is applied both to AV conducted and premature ventricular sensed events.

Although RV-only or LV-only sensing, denoted herein as univentricular sensing, may be combined with biventricular pacing, sensing in only one chamber increases the risk of competitive pacing, since pacing may be asynchronous in the unsensed chamber. For example, when RV-only sensing is used with right ventricular based timing and positive RV-LV interval, an undetected intrinsic left ventricular depolarization may be produced by a right ventricular pace or sense prior to the scheduled left ventricle pacing.

Figure 13:
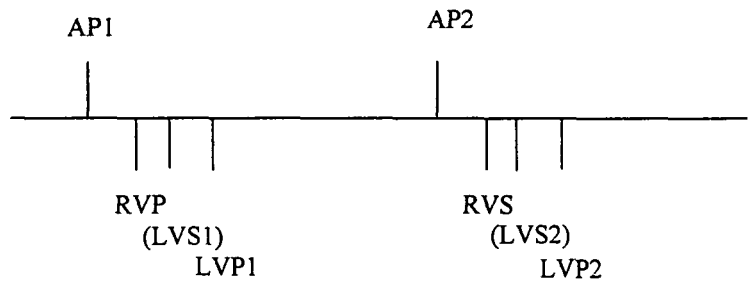
FIGS. 13 and 14 are timing diagrams illustrating competitive pacing in the situation of univentricular sensing combined with biventricular pacing.

Competitive pacing in the situation of univentricular sensing combined with biventricular pacing is illustrated in FIG. 13. In each cycle shown, the intrinsic left ventricular event (LVS1), (LVS2) is not sensed. Therefore, a left ventricular paced event LVP1, LVP2 follows an unsensed intrinsic left ventricular event (LVS1), (LVP2). If the left ventricular paced event LVP1, LVP2 closely follows the unsensed intrinsic left ventricular event (LVS1), (LVS2), the left ventricular paced event LVP1, LVP2 may not result in effective capture. In this situation, the left ventricular paced event LVP1, LVP2 would either encounter physiologically refractory tissue or, in the setting of a very delayed interventricular conduction, true fusion would result. It is unlikely that this type of competitive pacing wherein a chamber is paced closely following an intrinsic event in the chamber would induce a repetitive rhythm.

Figure 14:
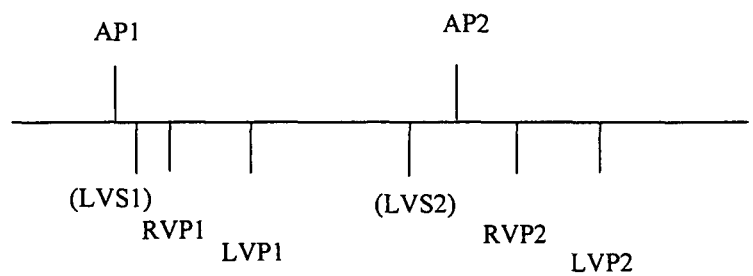

There is an even greater risk of competitive pacing when an unsensed depolarization occurs before pacing in a contralateral chamber upon which timing is based. Competitive pacing when an unsensed left ventricular depolarization occurs before right ventricular pacing, either in the AV interval or the VA interval, is illustrated in FIG. 14. In this example, right ventricle based timing is used. The risk of competitive pacing in this situation may increase when the intrinsic LV to RV conduction delay is prolonged and when a long positive RV-LV interval is programmed. As illustrated in FIG. 14, the left ventricular event (LVS1), (LVS2) precedes the contralateral paced event RVP1, RVP2. When a long RV-LV interval is present, and the LV-RV conduction is very prolonged, the left ventricle paced event LVP1, LVP2 may occur when the left ventricle is no longer refractory.

Figure 15:
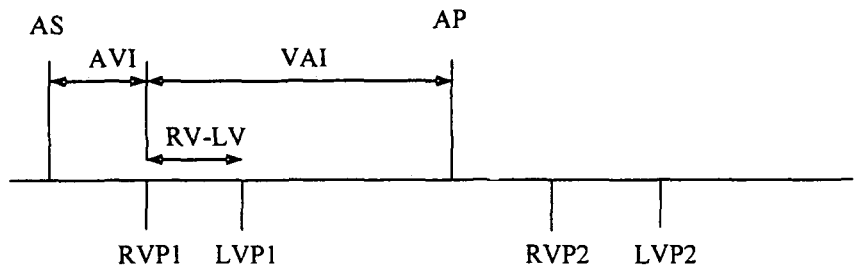
FIGS. 15-18 are a timing diagrams illustrating biventricular sensing and pacing combined with univentricular based timing in accordance with embodiments of the invention.

Biventricular sensing and pacing may be combined with univentricular based timing in several ways. Right ventricular based timing with a positive RV-LV interval in the absence of intrinsic conduction is illustrated in FIG. 15. Following a sensed or paced atrial event AS, AP, the right ventricle is paced RVP1, RVP2 following an AV interval AVI. The left ventricle may be paced LVP1, LVP2 in accordance with an established RV-LV interval.

Figure 16:
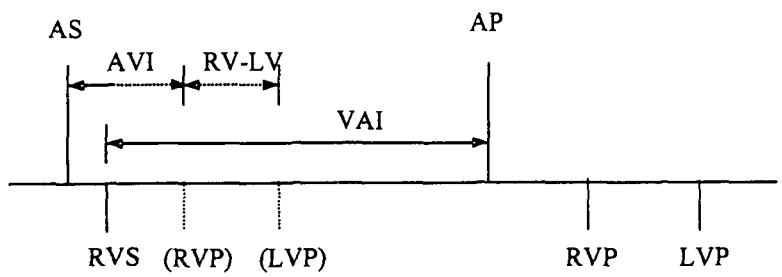

If an intrinsic right ventricular event occurs in the AV interval, there are several possibilities for resetting the pacing intervals. In one example, the intrinsic right ventricular event may reset all the pacing intervals so neither the right nor left ventricle is paced. This situation is illustrated in FIG. 16. The right ventricular sensed event RVS resets the timing cycle, creating a new VA interval VAI. The previously scheduled right ventricular and left ventricular paces are inhibited (RVP), (LVP).

Figure 17:
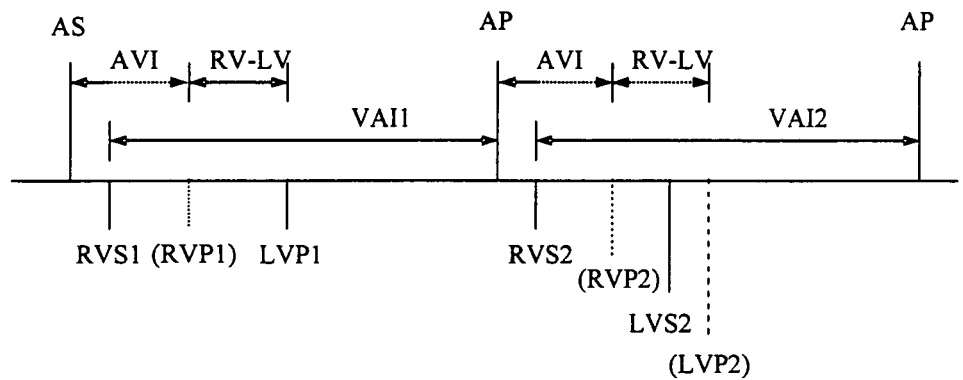

In another example, illustrated in FIG. 17, a right ventricular sense RVS1, RVS2 starts a new VA interval VAI1, VAI2 so the right ventricle is not paced at the scheduled time (RVP1), (RVP2). Left ventricle pacing LVP1 may occur, however, the left ventricular pace may be inhibited (LVP2) if it is preceded by an intrinsic left ventricular event LVS2.

Figure 18:
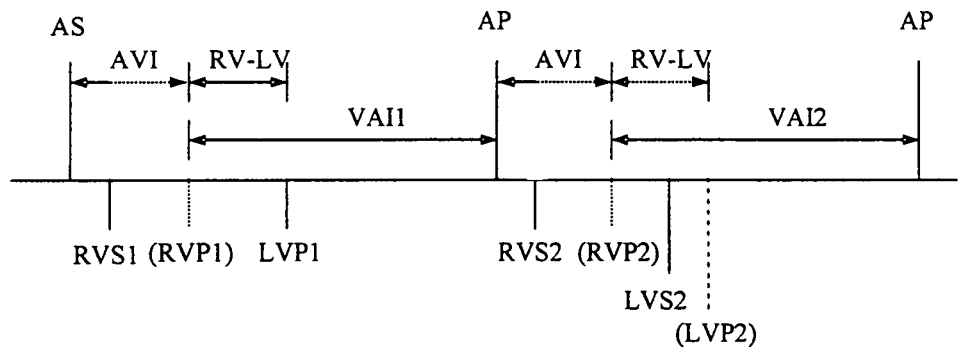

Furthermore, as illustrated in FIG. 18, a VA interval VAI1, VAI2 may be initiated from the theoretical point of delivery of an inhibited right ventricular pace (RVP1), (RVP2) at the end of the AV interval AVI. A left ventricular pace LVP1 may be delivered after the intrinsic right ventricular intrinsic event RVS1. However, in the event that an intrinsic left ventricular event is sensed LVS2, the left ventricular pace may be inhibited (LVP2).

Biventricular pacing may be used to synchronize right and left ventricular contractions. Synchronization may be enhanced through the use of a triggered response to biventricular sensing. A pace may be triggered, for example, in a heart chamber immediately following an intrinsic event in the contralateral chamber. Thus, triggered pacing may establish synchronized contractions of the two bilateral heart chambers.

Figure 19:
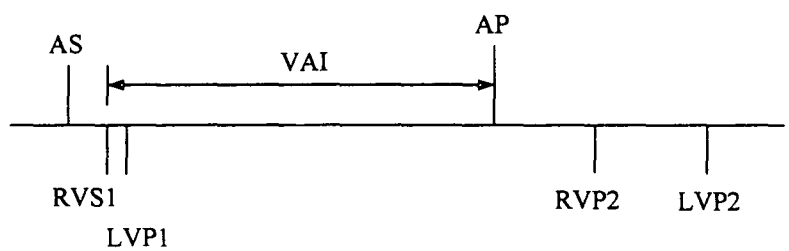
FIGS. 19-20 are timing diagrams illustrating triggered pacing in accordance with an embodiment of the invention.

In one example of triggered pacing, illustrated in FIG. 19, a right ventricular sense RVS1 immediately triggers a left ventricular pace LVP1. In this example, triggered pacing may be used to mitigate an abnormally prolonged intrinsic delay between ventricular contractions. If no intrinsic event is sensed in the right ventricle, the right and left ventricles are paced RVP2, LVP2 according to a programmed RV-LV interval.

Figure 20:
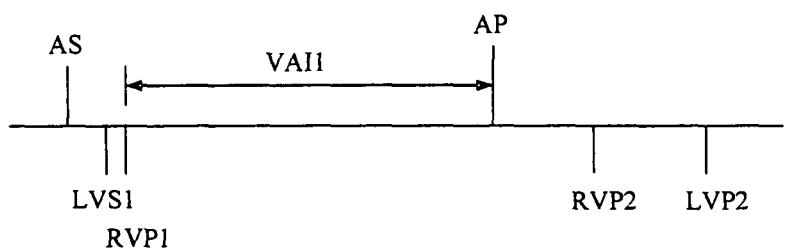

In another example of triggered pacing, illustrated in FIG. 20, a left ventricular sense LVS1 in the AV interval may trigger a right ventricular pace RVP1. If no intrinsic event is sensed, the right and left ventricles are paced RVP2, LVP2 according to a programmed RV-LV interval.

In another example, pacing may be triggered in a heart chamber following an intrinsic event in the contralateral chamber after some delay interval. In an example of this approach, a sense in a ventricular chamber may trigger a sensed RV-LV interval in a manner analogous to a sensed versus paced AV interval. The sensed RV-LV interval may have a different duration from a paced RV-LV interval used when the ventricular chamber is paced.

Figure 21:
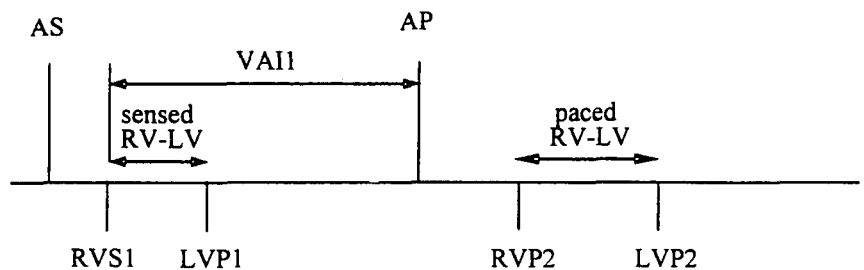
FIG. 21 is a timing diagram illustrating sensed and paced RV-LV intervals in accordance with an embodiment of the invention.

Sensed and paced RV-LV intervals are illustrated in FIG. 21. The right ventricular sense RVS1 illustrated in FIG. 21 triggers a sensed RV-LV interval. The sensed RV-LV interval is followed by a left ventricular pace LVP1. If no intrinsic right ventricular event is sensed, the right ventricle is paced RVP2. A paced RV-LV interval separates the right ventricular pace RVP2 from the left ventricular pace LVP2.

Figure 22:
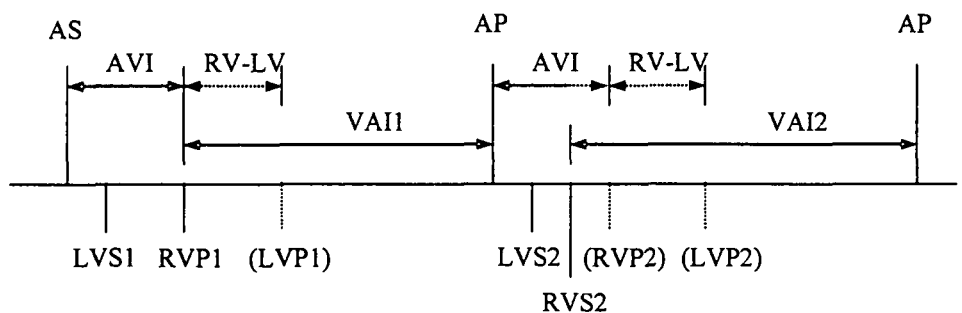
FIG. 22 is a timing diagram illustrating biventricular sensing with pacing upon sensing an intrinsic event in accordance with an embodiment of the invention.

FIG. 22 illustrates an example of biventricular sensing with pacing upon sensing an intrinsic event. When an intrinsic left ventricular event LVS1, LVS2 occurs in the AV or RV-LV interval before a left ventricular pace, the left ventricular pace is inhibited (LVP1), (LVP2). The right ventricular pace RVP1 is unaffected and initiates the VA interval VAI1. However, if left ventricle to right ventricle conduction occurs quickly enough, resulting in a conducted right ventricular sense RVS2 before the right ventricular pace is scheduled, the right ventricular pace may be inhibited (RVP2). In this situation, the sensed right ventricular event RVS2 initiates the VA interval VAI2.

As previously described, the timing interval RV-LV between biventricular paces may be positive, wherein the right ventricle is paced before the left ventricle, or the timing interval RV-LV may be negative, wherein the left ventricle is paced before the right ventricle. Analogous interaction of sensing to inhibit or trigger pacing is possible within a negative RV-LV interval. Thus, a right ventricular sense prior to the RV-LV interval, that is, before the left ventricular pace, could reset all the pacing intervals, including the VA interval and the RV-LV interval.

In another approach, a right ventricular sense prior to the RV-LV interval may reset only the VA interval, or trigger an immediate left ventricular pace. A right ventricular sense during the RV-LV interval, that is, following the left ventricular pace, may reset the VA interval and inhibit the scheduled right ventricular pace. A left ventricular sense prior to the left ventricular pace may inhibit the left ventricular pace, trigger an immediate right ventricular pace, or trigger a sensed RV-LV interval ending in an right ventricular pace.

A multichamber CFM device may be programmed to sense in two bilateral chambers while pacing in only one of the chambers. For example, a biventricular CFM device may be programmed for biventricular sensing while pacing in only one ventricle, for instance, left ventricle only pacing. In patients with delayed left ventricular conduction, such as left bundle branch block, it may be necessary to pace only the delayed left ventricle. However, because intrinsic conducted activity occurs first in the right ventricle, it might be advantageous to reset pacing intervals based on right ventricular sensed events, as well as left ventricular events.

Figure 23:
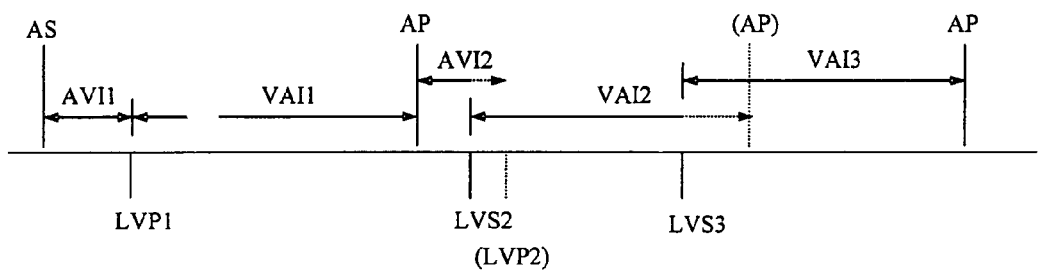
FIGS. 23-24 are timing diagrams illustrating sensing in both ventricles and pacing in one ventricle in accordance with an embodiment of the invention.

Representative examples of some possible timing cycles involving sensing in both ventricles and pacing in one ventricle are illustrated in FIG. 23. A left ventricular pace LVP1 following the AV interval AVI1 initiates the VA interval VAI1. If a left ventricular sensed event LVS2 occurs during the AV interval AVI2, left ventricular pacing may be inhibited (LVP2) and the VA interval VAI2 initiated by the left ventricular sensed event LVS2. If a left ventricular sensed event LVS3 occurs during a VA interval VAI2, the VA interval may be reset VAI3, inhibiting the scheduled atrial pace (AP).

Figure 24:
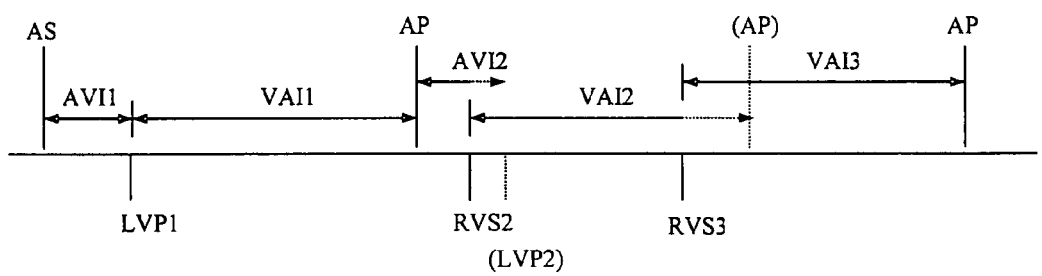

Furthermore, a right ventricular sensed event during the AV or VA intervals may inhibit pacing and reset the VA interval, as illustrated in FIG. 24. Examples of possible timing cycles involving a right ventricular sensed event are illustrated in FIG. 24. A left ventricular pace LVP1 following the AV interval AVI1 initiates the VA interval VAI1. If a right ventricular sensed event RVS2 occurs during the AV interval AVI2, left ventricular pacing may be inhibited (LVP2) and the VA interval VAI2 initiated by the right ventricular sensed event RVS2. If a right ventricular sensed event RVS3 occurs during a VA interval VAI2, the VA interval may be reset VAI3 by the right ventricular sensed event RVS3, inhibiting the scheduled atrial pace (AP).

Sensing in multichamber devices can also provide triggering for single chamber pacing modes. For example, biventricular sensing may utilize biventricular triggering to trigger pacing in a particular ventricle. For instance, with left ventricular only pacing and biventricular sensing, a premature right ventricular sense in the AV interval or in the VA interval could trigger an immediate left ventricular pace in an attempt to minimize the contraction delay between right and left ventricles.

Figure 25:
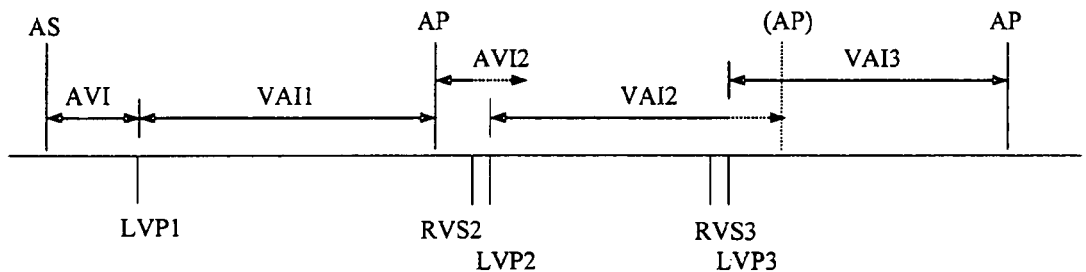
FIG. 25 is a timing diagram illustrating biventricular sensing and left ventricular pacing with triggering and left ventricle based timing in accordance with an embodiment of the invention.

FIG. 25 illustrates an example of biventricular sensing and left ventricular pacing with triggering and left ventricle based timing. A right ventricular sensed event RVS2 in the AV interval AVI2 triggers a left ventricular pace LVP2 initiating the VA interval VAI2. In addition, a sensed right ventricular event RVS3 in the VA interval VAI2 triggers an immediate left ventricular pace LVP3 and resets the VA interval VAI3.

Figure 26:
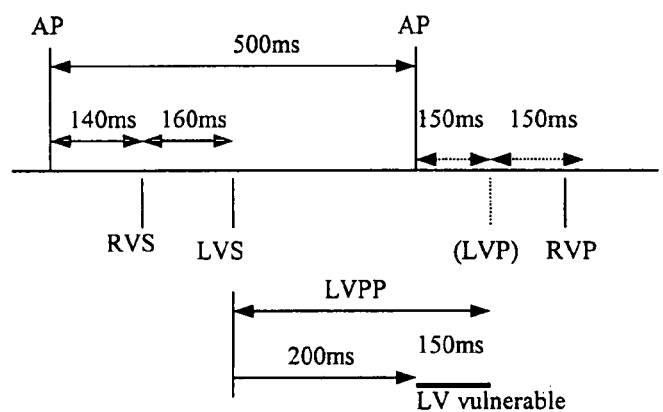
FIG. 26 illustrates a ventricular protection period in accordance with an embodiment of the invention.

Enforcing the maximum tracking rate interval may be used to prevent pacing the ventricles too fast. Another mitigating strategy to prevent pacing too fast is to initiate a protection period upon sensing a ventricular event that prevents pacing in that ventricle before the end of the period. For example, with RV based timing, RV pacing but not LV pacing is protected by the maximum tracking rate interval so LV pacing could be protected by a LV protection period LVPP. In the example of FIG. 26, the left ventricular protection period LVPP may be used to inhibit a left ventricular pulse (LVP) within a left ventricular protection period interval LVPP following a left ventricular sensed event LVS. This approach may decrease the likelihood of competitive pacing in the left ventricle when the left ventricle tissue is no longer refractory.

FIGS. 27-33 illustrate embodiments of the invention involving various combinations of pacing timing cycles for synchronized multisite pacing. Pacing timing cycles based on events occurring at a particular site or based on events occurring at either of two sites may be used to control pacing escape intervals and heart rate. Sensed events may also be used to trigger or inhibit pacing.

FIGS. 27A-33B are timing diagrams illustrating various pacing timing modes in accordance with embodiments of the invention. For example, a timing mode in accordance with an embodiment of the invention may include sensing in a first ventricle and pacing in both ventricles. A pacing escape interval may be initiated by a sensed or paced event occurring in the first ventricle.

In this situation, the pacing timing cycle is based on events occurring in a particular ventricle. The timing may be designated as left ventricle based timing or right ventricle based timing. These embodiments of pacing timing correspond to the BBR, BBL, BRR, and BLL biventricular pacing codes described in FIG. 9, wherein timing is designated as either right ventricle based timing or left ventricle based timing.

In one example of an embodiment of the invention, sensing is enabled in the right ventricle and pacing is enabled in the left and right ventricles, corresponding to a biventricular BRR pacing code. Thus, a sensed event in the right ventricle initiates a pacing escape interval. After the pacing escape interval expires, pacing in the right ventricle occurs. Pacing in the left ventricle occurs according to a timing interval from the right ventricular pace.

Alternatively, the left ventricle may be sensed and designated for timing, corresponding to the biventricular BLL pacing code described in FIG. 9. If left ventricle based timing is designated, a sensed event in the left ventricle initiates the pacing escape interval. Following expiration of the pacing escape interval, pacing in the left ventricle occurs. The right ventricle is paced according to a timing interval from the left ventricular pace.

Sensing may be enabled in both ventricles. Sensing in both ventricles corresponds to the BBR and BBL codes, wherein the last letter indicates the ventricle used for timing.

As previously described, the timing interval between the left and the right ventricle paces, denoted herein as the RV-LV interval, may be positive, negative or zero. A typical value for the RV-LV interval is about 100 ms.

In addition to pacing and sensing in the ventricles, pacing and/or sensing may be enabled in an atrial chamber. A right ventricular sense initiates a ventriculoatrial (VA) pacing escape interval VAI. Expiration of the VA escape interval triggers a paced event in the atrium. An atrioventricular AV pacing escape interval may be initiated by a sensed or paced event in the atrial chamber. Expiration of the AV pacing interval may trigger a paced event in the ventricles.

Pacing escape intervals may vary depending on whether the pacing escape intervals are initiated by a sensed or paced event. For example, the duration of a pacing escape interval initiated by a paced event at the first site may be different from the duration of a pacing escape interval initiated by a sensed event at the first site. More specifically, if the right ventricle is sensed, an intrinsic right ventricular event may initiate a pacing escape interval, for example a VA interval, of one particular duration, whereas a paced right ventricular event may initiate a pacing escape interval of the same duration or a different duration. In addition, the duration of the AV interval may vary depending on whether the AV interval was triggered by a sensed or a paced atrial event.

To reduce the possibility of competitive pacing, a protection period may be initiated upon sensing a cardiac event to prevent the site where the event is sensed from being paced during a vulnerable period. In another approach, a sensed event at one site may trigger a pace in the other site. For example, in the context of biventricular pacing, a right ventricular sense may trigger a left ventricular pace immediately or after a time interval. Conversely, a left ventricular sense may trigger a pace in the right ventricle.

As discussed previously, the maximum tracking rate may be enforced when the AV interval expires during the MTR interval in biventricular pacing modes. In one approach, for example, when the AV interval expires before the end of the maximum tracking rate interval MTRI, the scheduled ventricular pulse at the first pacing site is inhibited. Expiration of the MTRI interval triggers a pace at the first pacing site. This approach ensures that the maximum tracking rate is maintained.

Figure 27A:
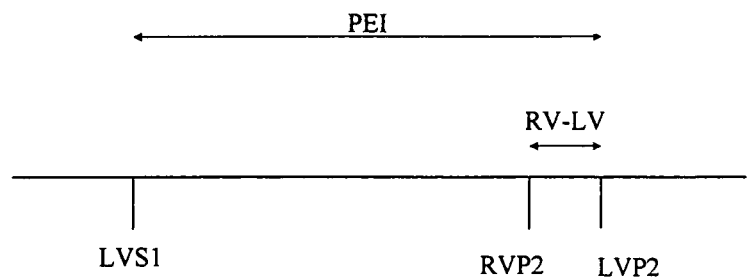
FIGS. 27A-33B are pacing timing diagrams illustrating pacing modes in accordance with embodiments of the invention.
Figure 27B:
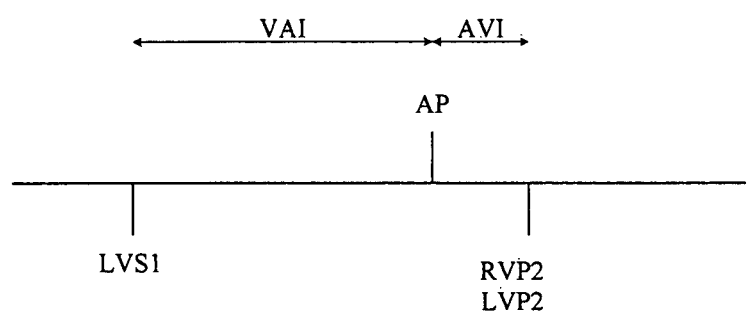
Figure 27C:
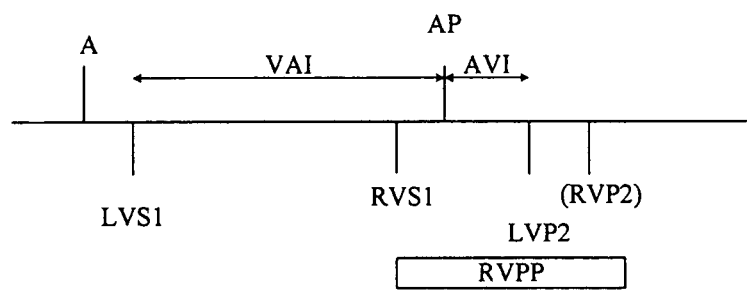

FIGS. 27A-27C illustrate example cardiac cycles involving sensing at least one ventricle and pacing one or both ventricles with timing based on a particular ventricle in accordance with the embodiment described above. In FIG. 27A, the timing is designated as left ventricular timing, thus, the left ventricle is sensed. A sensed event in the left ventricle LVS1 initiates the pacing escape interval PEI. Upon expiration of the pacing escape interval PEI, the left and right ventricles are paced RVP2, LVP2 according to a positive RV-LV interval. The left ventricular pace LVP2 resets the cardiac cycle.

In another approach, illustrated in FIG. 27B, the atrium is also paced. A sensed left ventricular event LVS1 initiates a VA interval VAI. After expiration of the VA interval VAI, the atrium is paced AP initiating an AV interval AVI. Upon expiration of the AV interval AVI, the left and right ventricles are paced simultaneously corresponding to an RV-LV interval of zero. The left ventricular pace initiates the VA interval.

FIG. 27C illustrates the use of a protection period when the second site is sensed and paced. In this particular example, left ventricular based timing is used with a negative RV-LV interval. As before, a sensed left ventricular event LVS1 initiates a VA interval VAI. After the VA interval expires, the atrium is paced and the AV interval begins. If a right ventricular event is sensed RVS1, a right ventricular protection period RVPP begins. Because the scheduled right ventricular pace falls within the right ventricular protection period RVPP, the scheduled right ventricular pace is inhibited (RVP2) preventing pacing the right ventricle during the vulnerable period.

FIGS. 27A-27C described above illustrate examples of timing cycles involving sensing at least one ventricle and pacing one or both ventricles with timing based on a particular ventricle. The examples illustrated represent only a few of the timing cycles that are possible using the pacing mode described.

Figure 28A:
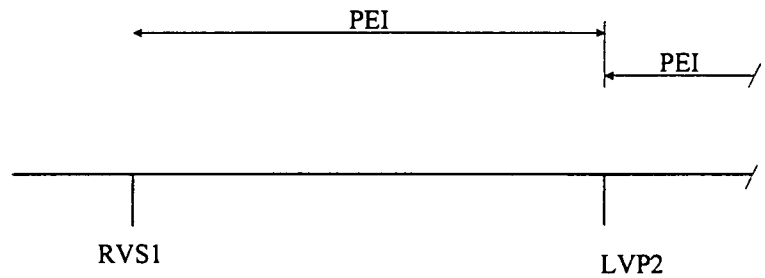
Figure 28B:
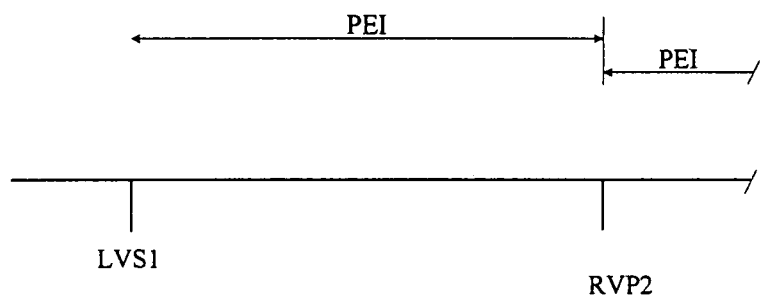
Figure 28C:
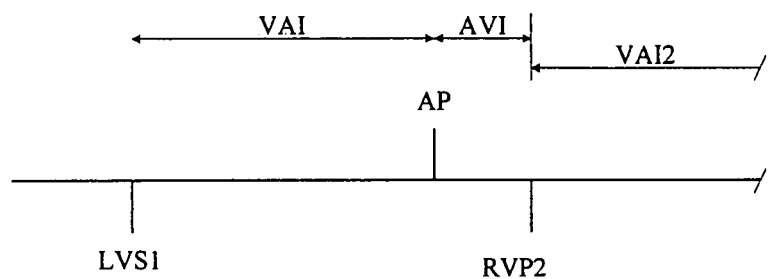

FIGS. 28A-28C illustrate examples involving sensing in at least one site and pacing at the opposite site in accordance with an embodiment of the present invention. In this example embodiment, a sensed event at one site or a paced event at a second site may initiate a pacing escape interval.

In the context of biventricular pacing, this approach corresponds to the RLB or LRB pacing modes described in FIG. 9 wherein one ventricular chamber is paced and the opposite chamber is sensed. FIG. 28A illustrates a pacing timing mode in accordance with this embodiment. A right ventricular sensed event initiates the pacing escape interval PEI. The left ventricle is paced LVP2 after the pacing escape interval expires and initiates the next pacing escape interval.

FIG. 28B illustrates this pacing approach when left ventricular sensing is used with right ventricular pacing. The left ventricular sense LVS1 initiates the pacing escape interval PEI. The right ventricle is paced RVP2 after the expiration of the pacing escape interval and initiates the next pacing escape interval.

In addition to sensing in one ventricular chamber, as described in FIGS. 28A and 28B, an atrial chamber may also be sensed. Thus, an atrioventricular pacing escape interval (AVI) may be initiated upon the occurrence of an atrial sensed or paced event. Expiration of the AV interval triggers pacing in the paced ventricular chamber. The duration of an AV interval may vary. For example, an AV interval initiated by a sensed atrial event may be different from the duration of the AV interval initiated by a paced atrial event. The situation wherein sensing and pacing is enabled in an atrium is illustrated in FIG. 28C.

In the example wherein an atrium is sensed and paced, a ventriculoatrial pacing escape interval VAI is initiated upon sensing the first ventricular site LVS1. Upon expiration of the VAI, the atrium may be paced AP and an AV pacing interval AVI is initiated. Upon expiration of the AV interval AVI, the right ventricle is paced RVP2 and initiates the next VA interval.

It is understood that although the examples described in connection with FIGS. 28A through 28C present biventricular approaches to multichamber pacing, the sensed and paced heart chambers may be atria. Furthermore, first and second sites within a particular heart chamber may be paced according to the timing cycles described herein.

Various approaches may modify the VA or AV pacing escape intervals, the order of pacing, and the inhibition or triggering of paced events. In one approach, the duration of a pacing escape interval initiated by a pace at the first site may be different from the duration of a pacing escape interval initiated by a sensed event at the second site. For example, if the right ventricle is sensed, an intrinsic right ventricular event may initiate a pacing escape interval of one particular duration, whereas a paced left ventricular event may initiate a pacing escape interval of the same duration or a different duration.

Furthermore, sensing can be enabled in the site that is pace to prevent competitive pacing. A sensed event at the paced site may initiate a protection period during which a paced event at that site is inhibited as previously described, but the theoretical time when the site would be paced initiates the next pacing escape interval. Alternatively, or additionally, a sensed event at the one site may trigger a paced event at the other site. For example, a sensed event in the right ventricle may trigger a paced event in the left ventricle. Similarly, a sensed event in the left ventricle may trigger a corresponding paced event in the right ventricle.

The maximum tracking rate may be enforced when the AV interval expires during the MTR interval in RLB and RLB pacing modes. In one approach, for example, when the AV interval expires before the end of the maximum tracking rate interval MTRI, the scheduled ventricular pulse at the pacing site is inhibited. Expiration of the MTRI interval triggers a pace at the pacing site. This approach ensures that the maximum tracking rate is maintained.

In accordance with one embodiment of the invention, sensing at one site and pacing at two sites, as described in FIG. 9 as BRB and BLB pacing modes, is illustrated in FIGS. 29A-29D. In this embodiment, the pacing escape interval is initiated by either a sensed event at a first site or paced event at the opposite site.

Figure 29A:
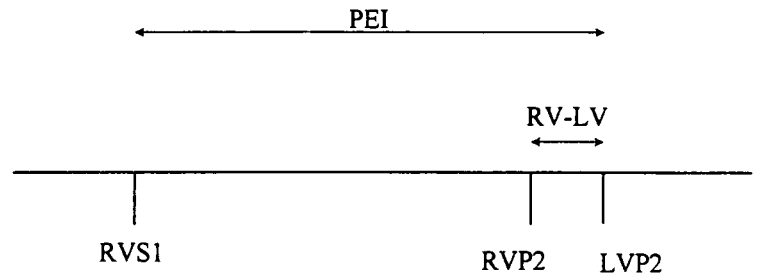
Figure 29B:
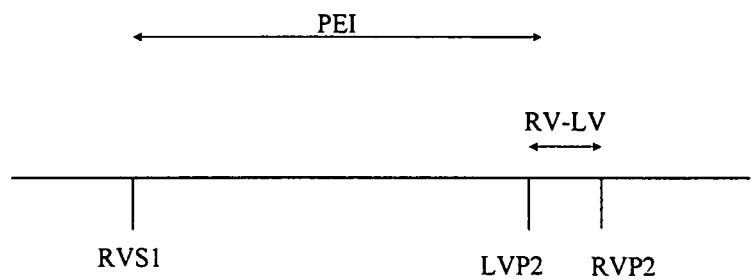

FIGS. 29A-29D, illustrate various examples of pacing timing cycles involving sensing at one site and pacing at two sites. In the illustration of FIG. 29A, the right ventricle is used as the sensed site. A sensed event in the right atrium RVS1 initiates a pacing escape interval. Upon expiration of the pacing escape interval PEI, the left ventricle is paced followed by a right ventricular pace. The left ventricular pace resets the pacing escape interval. FIG. 29B illustrates an example, wherein the left ventricle is paced first LVP2 restarting the pacing escape interval.

Figure 29C:
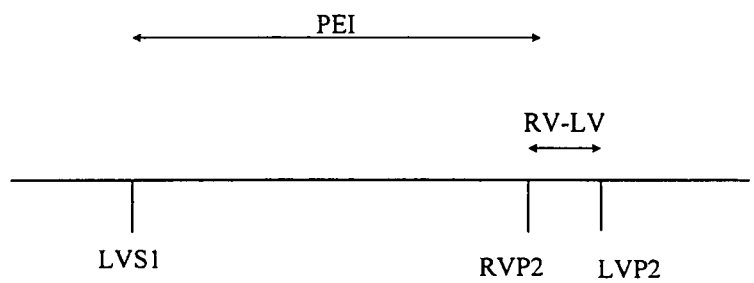
Figure 29D:
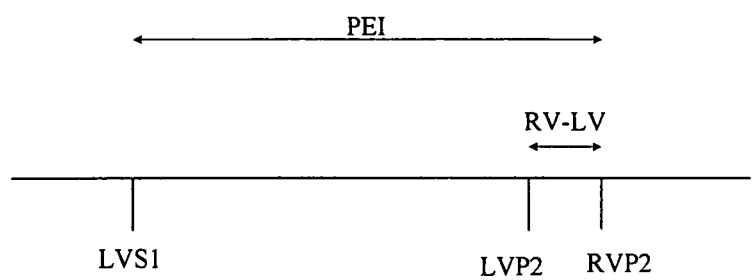

FIGS. 29C-29D illustrate examples in which the left ventricle is sensed. If there is a positive RV-LV interval, the right ventricle is paced first followed by the left ventricular pace, as in FIG. 29C, and the right ventricle resets the pacing escape interval. If there is a negative RV-LV interval, the left ventricle is paced first, followed by the right ventricular pace corresponding to FIG. 29D, and the right ventricular pace resets the pacing escape interval.

The RV-LV interval may be positive wherein the right ventricular pace precedes the left ventricular pace as previously discussed in connection with FIGS. 29A and 29C. The RV-LV interval may be negative with the right ventricular pace following the left ventricular pace, as previously discussed in connection with FIGS. 29B and 29D. When the left and right ventricles are paced simultaneously, the RV-LV interval is zero. A typical RV-LV interval is about 100 ms.

In addition to sensing and pacing the ventricles, an atrial chamber may also be sensed and paced in a manner similar to the examples previously described. For example, a sensed right ventricular event initiates a VA interval. When the VA interval expires, the atrium is paced and the AV interval is initiated. Although in this example, the AV interval is commenced by an atrial pace, the AV interval could also be initiated by a sensed event in the atrium. Furthermore, the duration of the AV interval could be different for atrial sensed and paced events. Upon the expiration of the AV interval, the left and right ventricles are paced.

When the pacing escape interval, for example, the AV interval expires before the end of the maximum tracking rate interval, the scheduled ventricular pace may inhibited to maintain tracking. The ventricular pace may be delivered following the expiration of the maximum tracking rate interval.

In addition, a sensed event at a site that is paced and used for timing may initiate a protection period during which a paced event at the site is inhibited. Further, triggering may be used wherein a sensed event at one site may trigger a paced event at the other site.

Pacing cycles in accordance with a further example of an embodiment of the invention with BRB and BLB timing modes are illustrated in FIGS. 30A-30D. In these examples, the pacing escape interval is initiated by a sensed event at a first site or a first paced event at a first site or a second site. The chamber not paced by the first paced event is paced after an RV-LV interval, which may be zero, initiated by the first paced event.

Figure 30A:
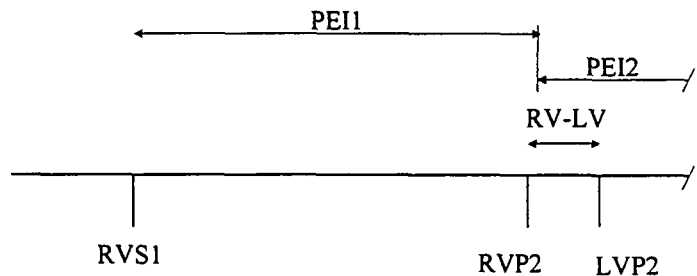

For example, a biventricular timing mode may involve sensing a right ventricle and pacing the left and right ventricles with the right ventricle designated as the first paced site as illustrated in FIG. 30A. After the right ventricle event is sensed RVS1, a pacing escape interval PEI1 is initiated. After the pacing escape interval PEI1 expires, the right ventricle is paced RVP2. The left ventricle is paced LVP2 after an RV-LV interval initiated by the right ventricular pace The right ventricular pace resets the VA interval VAI2.

Figure 30B:
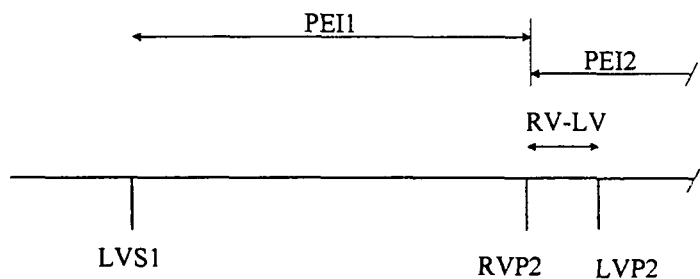

Alternatively, the timing mode may involve sensing the left ventricle and pacing the right and left ventricles, as illustrated in FIG. 30B, with the right ventricle designated as the first paced site. In this example, the left ventricular sense LVS1 begins a pacing escape interval PEI1. After expiration of the pacing escape interval PEI1, the right ventricle is paced RVP2, which initiates the next pacing escape interval PEI2. The left ventricle is paced LVP2 after an RV-LV interval initiated by the right ventricular pace.

Figure 30C:
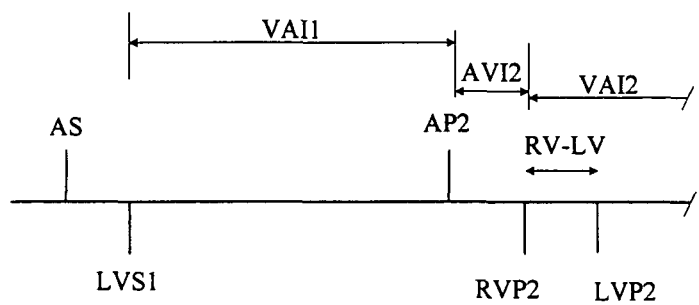

In addition to sensing and pacing the ventricles, an atrial chamber may also be sensed and paced in a manner similar to the examples previously described. An example embodiment is illustrated in FIG. 30C, involving sensing the left ventricle and pacing the right and left ventricles, with the right ventricle designated as the first paced site. A left ventricular sense LVS1 initiates a VA delay interval VAI1. After expiration of the VA interval VAI1, the atrium is paced AP2 and an AV interval AVI2 is initiated. After the AV interval AVI2 expires, the right ventricle is paced RVP2 initiating another VA interval VAI2. The left ventricle is paced LVP2 after an RV-LV interval.

Figure 30D:
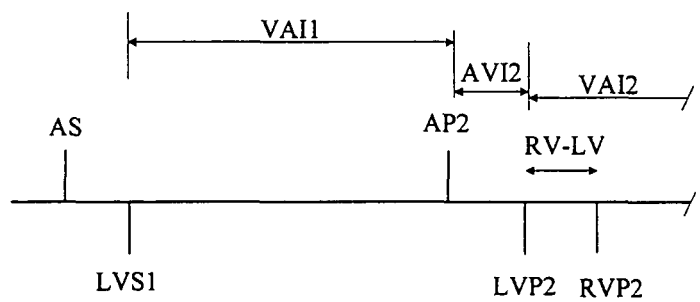

Another example is illustrated in FIG. 30D, involving sensing the left ventricle and pacing the right and left ventricles, with the left ventricle designated as the first paced site. A left ventricular sense LVS1 initiates a VA delay interval VAI1. After expiration of the VA interval VAI1, the atrium is paced AP2 and an AV interval AVI2 is initiated. After the AV interval AVI2 expires, the left ventricle is paced LVP2 initiating another VA interval VAI2. The right ventricle is paced RVP2 in accordance with a negative RV-LV interval.

In accordance with another embodiment of the invention, sensing at two sites may be combined with pacing at one site. In one example of this type of pacing mode, the pacing escape interval may be initiated by a first sensed event in either of a first or a second site or a paced event at the first site. Biventricular pacing modes that may operate by this approach include the RBB and LBB pacing modes described in FIG. 9.

For example, the first site may be the right ventricle and the second site may be the left ventricle. The pacing escape interval may be initiated by a first sensed ventricular event, whether deriving from the right ventricle or the left ventricle. The pacing escape interval may additionally be initiated by a paced event in the right ventricle, for example.

Figure 31A:
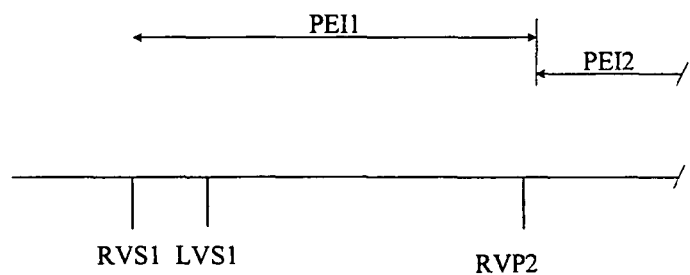

Various aspects of the example described in the above paragraph are illustrated in FIGS. 31A-31D. In FIGS. 31A-31D, the right ventricle is designated as the first site and the left ventricle is designated as the second site. In FIG. 31A, the first sensed event occurs in the right ventricle RVS1. Sensing the right ventricular event RVS1 initiates a pacing escape interval PEI1. Upon expiration of the pacing escape interval PEI1, the right ventricle is paced RVP2.

Figure 31B:
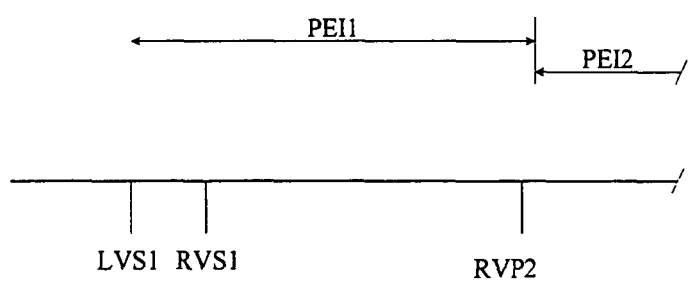

If a left ventricular sensed event occurs first, as illustrated in FIG. 31B, the pacing escape interval PEI1 is initiated upon sensing the left ventricular event LVS1. Upon expiration of the pacing escape interval PEI1, the right ventricle is paced RVP2.

Figure 31C:
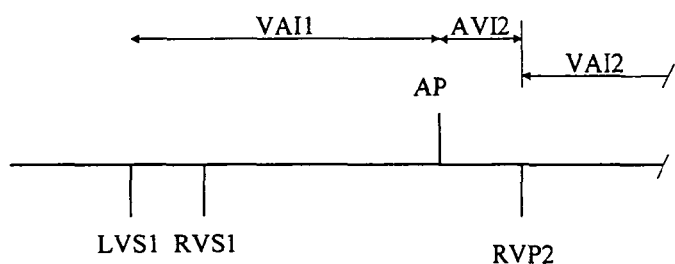

In addition to sensing in both ventricles and pacing in one ventricle, the atrium may also be sensed and paced, as illustrated in FIG. 31C. For example, a first occurring sensed left ventricular event LSV1 initiates a VA interval VAI1. When the VA interval VAI1 expires, the atrium is paced AP and an AV interval AVI2 begins. Although in this example, the AV interval AVI2 is commenced by an atrial pace, the AV interval could also be initiated by a sensed event in the atrium. Furthermore, the duration of the AV interval could be different for atrial sensed and paced events. Upon the expiration of the AV interval AVI2, the right ventricle is paced RVP2 initiating a new VA interval VAI2.

Figure 31D:
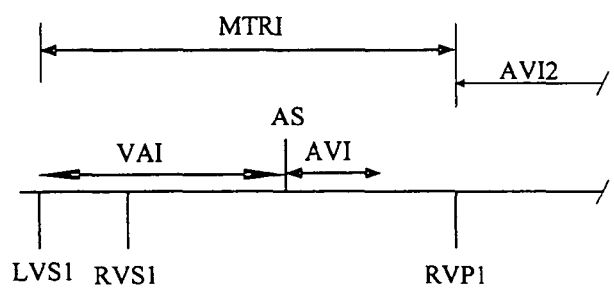

As illustrated in FIG. 31D, if the pacing escape interval, for example, the AV interval AVI, expires before the end of the maximum tracking rate interval MTRI, the scheduled ventricular pace may be inhibited to maintain tracking as described in connection with the above examples. The ventricular pace RVP1 may be delivered following the expiration of the maximum tracking rate interval MTRI, initiated by the first sensed event LVS1 as illustrated in FIG. 31D. The ventricular pace RVP1 initiates a VA interval VAI2.

In addition, a sensed event that does not initiate a pacing escape interval may be used to initiate a protection period for the chamber in which the event is sensed. During the protection period, a scheduled paced event in the chamber may be inhibited. In this example, a sensed event at the first site may initiate a protection period during which a paced event at the first site is inhibited. Further, triggering may be used wherein a sensed event at the second site may trigger a paced event at the first site.

Figure 32A:
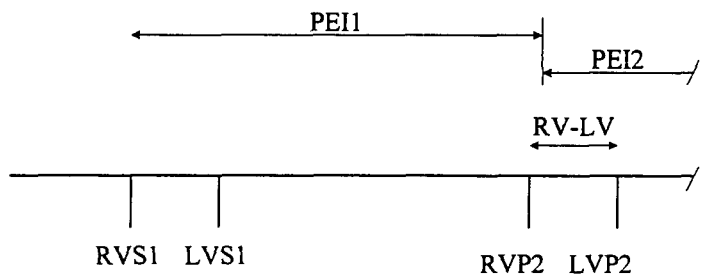
Figure 32B:
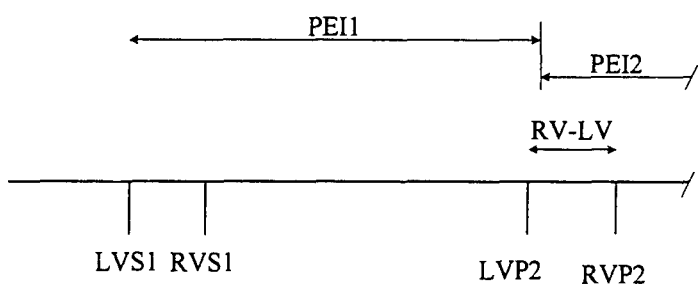
Figure 32C:
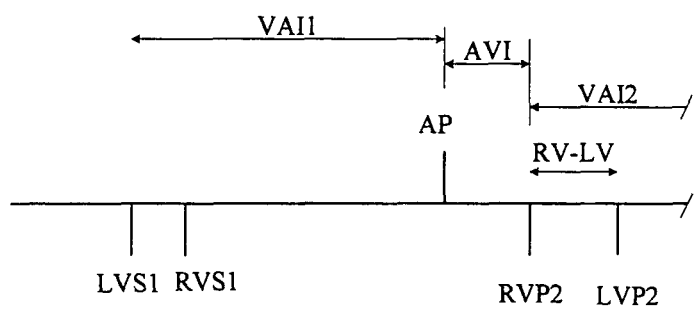

Another embodiment of the invention involves sensing and pacing in two cardiac sites, and a pacing escape interval is initiated by the first occurring sensed event at either the first or the second site, or a paced event at the first site. The second site is paced with an RV-LV interval from a pacing event at the first site. Examples of the pacing timing arranged according to this embodiment are illustrated in FIGS. 32A-32C. With regard to biventricular pacing, this embodiment corresponds to the pacing timing mode designated BBB in FIG. 9.

In FIGS. 32A-32C, the right ventricle is designated as the first site and the left ventricle is designated as the second site. A first occurring sensed event RVS1 initiates the pacing escape interval PEI1 as illustrated in FIG. 32A. Upon expiration of the pacing escape interval PEI1, the right ventricle is paced RVP2 and a pacing escape interval PEI2 is initiated. The left ventricle is paced LVP2 following a positive RV-LV interval from the right ventricular pace RVP2.

If the first occurring sensed event occurs in the left ventricle LVS1, as illustrated in FIG. 32B, then the left ventricular sensed event LVS1 initiates the pacing escape interval PEI1. When the pacing escape interval PEI1 expires, in this example, the left ventricle is paced LVP2, with the right ventricular pace RVP2 occurring according to a negative interval RV-LV. The left ventricular pace LVP2 initiates a new VA interval VAI2.

In addition to sensing and pacing in both ventricles, the atrium may also be sensed and paced, as illustrated in FIG. 32C. For example, a first occurring sensed left ventricular event LSV1 initiates a VA interval VAI1. When the VA interval VAI1 expires, the atrium is paced AP and an AV interval AVI begins. Although in this example, the AV interval AVI is commenced by an atrial pace, the AV interval could also be initiated by a sensed event in the atrium. Furthermore, the duration of the AV interval could be different for atrial sensed and paced events. Upon the expiration of the AV interval AVI, the right ventricle is paced RVP2 and the left ventricle is paced LVP2 according to a positive RV-LV interval.

In a further approach involving sensing and pacing in two cardiac sites, a pacing escape interval may by initiated by the first occurring sensed or paced event at either the first or the second site. Upon expiration of the pacing escape interval, the first paced site is paced followed by the second paced site after an RV-LV interval.

Figure 33A:
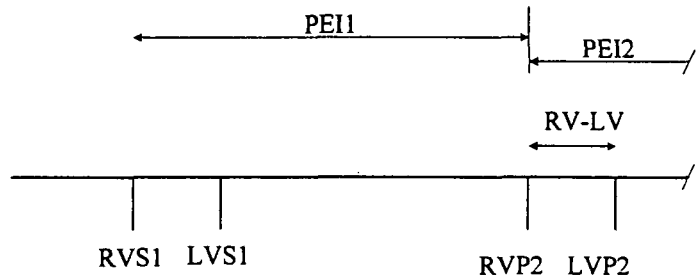
Figure 33B:
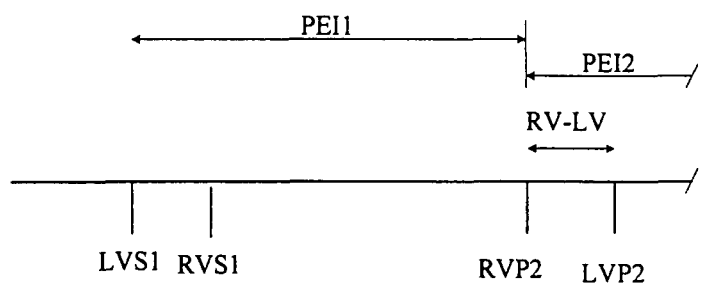

This approach is another example corresponding to biventricular pacing mode BBB designated in FIG. 9. Examples of this approach are illustrated in FIGS. 33A and 33B In these examples, the right ventricle is selected as the first paced site. In FIG. 33A, the first occurring sensed event is detected in the right ventricle RVS1. The right ventricular event initiates the pacing escape interval PEI1. When the pacing escape interval expires, the right ventricle is paced RVP2 followed after an RV-LV delay by the left ventricular pace LVP2. The right ventricular pace RVP2 initiates a pacing escape interval PEI2.

As illustrated in FIG. 33B, if a sensed event first occurs in the left ventricle LVS1, the left ventricular event initiates the pacing escape interval PEI1. Upon expiration of the pacing escape interval PEI1, the right and left ventricles are paced RVP2, LVP2. A RV-LV interval separates the pacing of the right and the left ventricles. The RV-LV interval may be dependent on a number of factors, including which ventricle is paced first, or whether the pacing interval is initiated by a paced or sensed event, for example. The right ventricular pace initiates a pacing escape interval PEI2.

In addition to pacing and sensing in both ventricles, one or both atria may also be paced and sensed. In this situation, pacing may be configured in a similar manner to the examples provided above.

It is apparent from the numerous examples presented above that timing based on biventricular sensing, or more generally multiple site sensing, enhances the ability to identify groups of cardiac events associated with a particular depolarization wavefront detected at the replicate sensing sites. For instance, this may be necessary to identify whether a right ventricular sense and a left ventricular sense are conducted from the atrium or are initiated as a result of a premature ventricular contraction. This is particularly difficult when a sequence of right and left ventricular senses occur in a row due to a series of depolarizations that are independently initiated.

Once initiated, a depolarization wavefront is conducted through the myocardium from the initiating site to all other connected regions in the activated chamber or chambers. When there are two or more sensing sites in the chamber or chambers, a depolarization wavefront will cause a sense event to be detected at each sensing site in a sequence determined by the spreading pattern and speed of the wavefront. Timing based on biventricular sensing, or more generally multisite sensing, enhances identifying the group of cardiac events associated with localized depolarizations of cardiac tissue occurring at the multiple sensing sites as the depolarization wavefront travels throughout the myocardium.

Figure 34A:
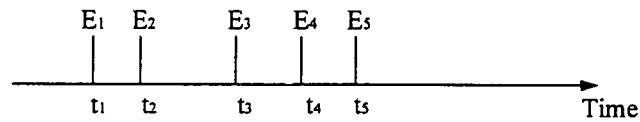
FIGS. 34A-F illustrate pairing states in accordance with embodiments of the invention.

The timing of cardiac events associated with a depolarization wavefront is illustrated in FIG. 34A. In this example, five cardiac sites are sensed. An event $E_1$ is detected in the first site reached by the depolarization wavefront at time $t_1$. The depolarization wavefront travels through the cardiac tissue causing detection of localized depolarization events $E_2$, $E_3$, $E_4$, $E_5$ at the remaining four sensing sites detected at times $t_2$, $t_3$, $t_4$, $t_5$.

In a more specific example, the sensed sites may be a single cardiac site in each of two bilateral heart chambers, such as a right and a left ventricle. A depolarization initiated in the right ventricle first may be detected at a time $t_1$, followed by a cardiac event detected in the left ventricle at time $t_2$. The period between $t_1$ and $t_2$ represents the time it takes for the depolarization wavefront to travel from the right to the left ventricle.

Alternatively, the depolarization could occur in the left ventricle first and travel to the right ventricle causing a cardiac event to be detected at the right ventricular site.

Identifying a group of sense events from replicate sensing sites associated with a depolarization wavefront may be accomplished by establishing a pairing state during which the first sensed events detected at each sensing site are identified as being associated with the same depolarization wavefront. Thus, the group of cardiac events associated with a depolarization wavefront includes a cardiac event detected at each sensing site.

The pairing state may be initiated upon the detection of the first cardiac event at any site that is not in a pairing state, that is, which is a first unpaired event. In addition, the pairing state may be initiated by a first pace pulse delivered at one of the sites. In this case, it is the pace pulse that initiates the depolarization wavefront. As the depolarization wavefront travels through the cardiac tissue, cardiac events are sensed at each of the remaining cardiac sites. When a cardiac event from each cardiac site has been detected, the group is complete and the pairing state for the depolarization wavefront may be terminated.

Figure 34B:
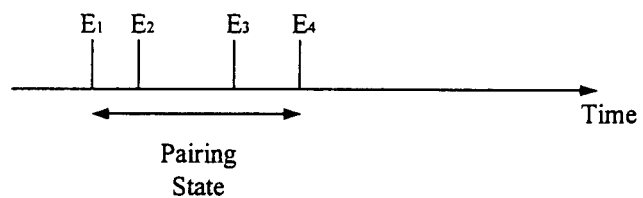

A pairing state, in accordance with an embodiment of the invention, is illustrated in FIG. 34B. In this example, cardiac events are associated with four sensing sites. A pairing state PS is associated with an interval of time, which may be referred to as a pairing interval, during which cardiac events $E_1$, $E_2$, $E_3$, $E_4$ are detected at each of the sensing sites.

In some situations, two independent depolarization wavefronts may be initiated at or near the same time and propagate simultaneously through the myocardium. In this case, it is possible that a second wavefront is detected at a single sensing site after a first wavefront has been detected but before the first wavefront has propagated to all the other sensing sites. Then two cardiac events associated with a single sensing site may be detected within a pairing state. The detection of a second cardiac event associated with a single site indicates that a second depolarization wavefront has been initiated before the group of cardiac events associated with the first depolarization wavefront has been identified. In this situation, the first pairing state may be terminated and a second pairing state initiated upon detection of the second cardiac event at the single site.

Figure 34C:
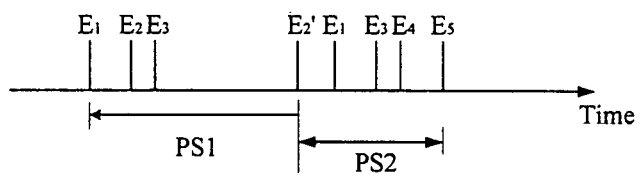

FIG. 34C illustrates the effect of an intervening second cardiac event on a pairing state in accordance with one embodiment involving sensing at five sites. A first pairing state PS1 is initiated by a first unpaired event $E_1$. Cardiac events $E_2$, and $E_3$, are detected during the first pairing state PS1. An intervening second cardiac event $E_2$, is detected at the second site during the first pairing state PS1 before cardiac events $E_4$ and $E_5$ are detected. Detection of the intervening second cardiac event $E_2'$ causes the first pairing state PS1 to be terminated. A second pairing state PS2 may be commenced using the second cardiac event $E_2'$ as the first unpaired event initiating the second pairing state PS2.

Figure 34D:
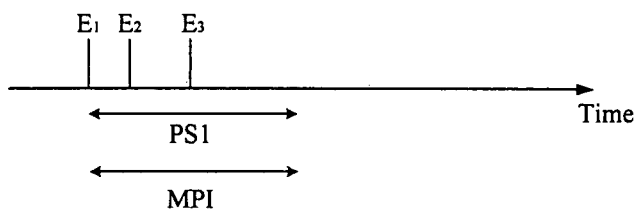

A pairing state may also be terminated if the group of cardiac events associated with a particular depolarization wavefront are not detected within a predetermined time interval, denoted herein as a maximum pairing interval. In the timing diagram illustrated in FIG. 34D five cardiac sites are sensed. A pairing state PS1 is initiated by a first unpaired event $E_1$. Cardiac events $E_2$, and $E_3$, are detected during the pairing state PS1. No additional cardiac events are detected during the pairing state PS1. The pairing state is terminated after a maximum pairing interval MPI has elapsed.

As discussed in more detail above, cardiac events associated with a particular site may be used to initiate timing cycles for pacing therapy. In biventricular sensing, and more generally in multisite sensing, particular cardiac events associated with a depolarization wavefront may be used to establish pacing timing cycles. For example, in the situation of biventricular sensing, cardiac events detected in the left ventricle may be used to initiate a pacing escape interval in LV based timing. Similarly, cardiac events detected in the right ventricle may be used to initiate a pacing escape interval in RV based timing. Furthermore, the first sensed cardiac events of the depolarization wavefront, that is, the first unpaired sense of an identified group, whether detected at the right ventricle or the left ventricle, may be used to initiate a pacing escape interval.

In another example embodiment of the invention, a pairing state and associated maximum pairing interval are used to reduce erroneous detection of opposite chamber events as premature contractions. The pairing state and maximum pairing interval are initiated on the first unpaired sense so that if an opposite chamber sense occurs during the maximum pairing interval, the two senses are detected as paired events. With this approach a premature ventricular contraction, for example, would be defined as a group of ventricular sensed cardiac events wherein the first unpaired sense occurring in the VA interval.

Figure 34E:
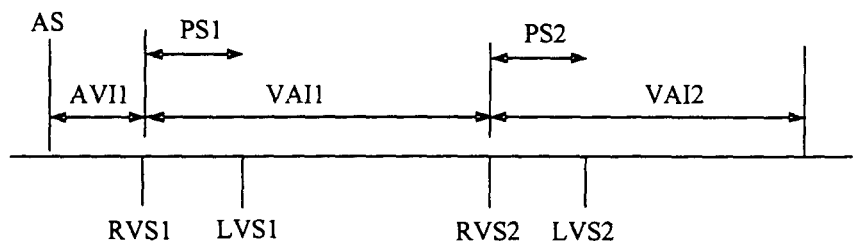

An example situation, illustrated in FIG. 34E, involves biventricular sensing with RV based timing. A VA escape interval VAI1 is initiated upon the detection of a right ventricular cardiac event RVS1. The right ventricular event RVS1 is a first unpaired sense and thus initiates a pairing state PS1 during which the depolarization started in the right ventricle travels to the left ventricle causing a localized depolarization in the left ventricle detected as a left ventricular sense LVS1. After the detection of the left ventricular sense, the pairing state PS1 initiated by the right ventricular event RVS1 is complete.

A second depolarization wavefront that is initiated within the VA interval VAI1 is a premature ventricular contraction. In this example, the second depolarization begins with a second right ventricular sense RVS2 within the VA interval VAI1. The second right ventricular sense RVS2 is a first unpaired sense that initiates a second pairing state PS2. The depolarization wavefront initiated by the second right ventricular sense RVS2 travels to the left ventricle and is detected as a left ventricular sense LVS2. Detection of LVS2 ends the pairing state PS2.

The group of cardiac events RVS2 and LVS2 that occur during the VA interval VAI1 is identified as a premature ventricular contraction, because the first unpaired sense RVS2 of the group, was detected during the VA interval VAI1. Identification of the premature ventricular contraction may be used to reset the VA interval VAI2, in this example, using the first unpaired sense RVS2 in the VA interval VAI1 to initiate the new VA interval VAI2.

Figure 34F:
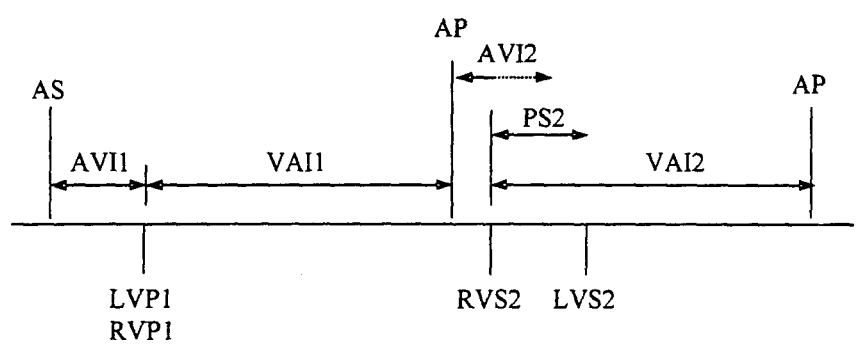

When both ventricles are sensed, either the right or left ventricular sense may fall outside of the AV interval, even on AV-conducted beats. The second ventricular sense does not necessarily represent a premature contraction because the second ventricular sense may be associated with the depolarization conducted from the atrium. FIG. 34F illustrates an example of biventricular sensing with zero RV-LV interval and right ventricle based timing. If the AV conduction occurs slightly early so a right ventricular sense RVS2 breaks though during the AV delay, the AV delay is terminated and the VA interval VAI2 is initiated. The right ventricular sense initiates a pairing state PS2.

Following an intrinsic RV-LV delay, which can be considerable in patients with ventricular conduction defects, a left ventricular sense LVS2 occurs during the VA interval VAI2 terminating the pairing state. Although the left ventricular sensed event LVS2 is a ventricular event occurring within the VA interval, in this example it does not represent a premature ventricular contraction (PVC) because the sensed event LVS2 is paired to the RV sense RVS2 and should not be used to reset the VA interval.

Figure 35:
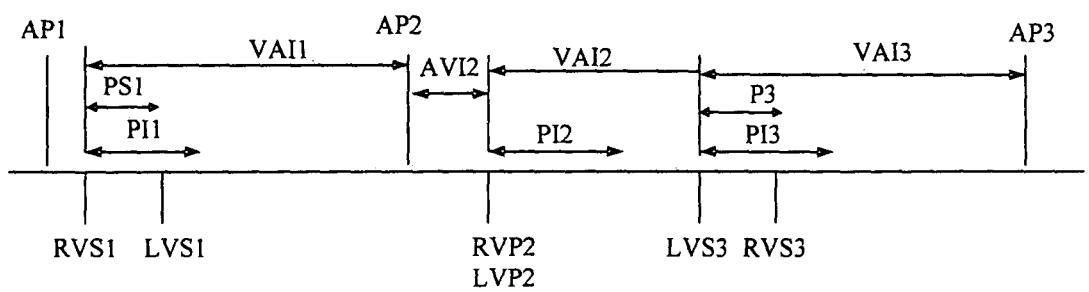
FIG. 35 illustrates pairing intervals in accordance with an embodiment of the invention.

FIG. 35 illustrates PVC detection using a maximum pairing interval. Following an atrial event AP1, a left ventricular sense LVS1 following a right ventricular sense RVS1 that initiates the VA interval VAI1 is not detected as a premature ventricular contraction so long as the left and the right ventricular events are paired in the pairing state PS1. In this example, the left ventricular event occurs within a maximum pairing interval PI1 after the occurrence of the right ventricular event RVS1.

In the second cycle, both the left and the right ventricles are paced simultaneously RVP2, LVP2 thereby initiating the VA interval VAI2 and a first pairing state in the VA interval associated with a maximum pairing interval P12. A left ventricular contraction is sensed LVS3 falling outside the maximum pairing interval P12. Because the left ventricular contraction LVS3 falls outside the pairing interval P12, it is detected as a first unpaired sense, and it resets the VA interval VAI3. The left ventricular contraction LVS3 also initiates a new pairing state associated with a maximum pairing interval P13. A right ventricular contraction RVS3 falling within the maximum pairing interval P13 does not reset the VA interval VAI3.

The use of pairing intervals for PVC detection may be configured in a number of ways depending on the type of timing desired or required. In one configuration associated with right ventricular based timing, a right ventricular sense of the PVC resets the VA interval. In another configuration associated with left ventricular based timing, a left ventricular sense resets the VA interval. In biventricular based timing, either of the paired PVC senses may reset the pacing intervals, and the timing response to PVC sensing may differ from the response to ventricular sensing during the AV or RV-LV intervals.

A cross-chamber refractory period may be used in a similar manner to the maximum pairing interval technique discussed above to reduce the detection of an AV conducted opposite chamber sense as a premature complex. The cross-chamber refractory period may be started after the first sense so that the opposite chamber sense is not detected. If the opposite chamber event occurs within the cross-chamber refractory period, the opposite chamber sense will not be detected as a premature contraction. However, there is some potential that the undetected opposite chamber sense might result in asynchronous pacing.

One approach to biventricular timing involves using triggering pacing in an opposite chamber whenever sensing occurs. In one example, a biventricular triggered mode is used to pace the opposite ventricle when a contraction is detected. In this example, any ventricular sense occurring during the AV or RV-LV intervals will trigger an opposite ventricular chamber pace if that chamber has not already been paced. This prevents a paired chamber sense from occurring in the VA interval after intrinsic AV conduction.

Biventricular triggering may be initiated by sensed premature ventricular contractions (PVC). Biventricular triggering for PVCs may follow the same or different timing conventions as biventricular triggering for AV conducted ventricular events as discussed above. As an example of a different convention for terminating PVCs, it may be important to trigger an immediate pace in the opposite chamber for whichever ventricular chamber is sensed first to start a collision wavefront that might prevent re-entrant excitation. Specific coupling intervals may be programmed to optimize this function. Triggered pacing on PVCs may require a maximum pacing rate limit and/or a limit on the number of sequential PVCs that trigger pacing in the opposite chamber.

As in atrioventricular pacing, refractory periods are required during biventricular sensing to prevent oversensing pacing artifacts. A right ventricular paced event or a left ventricular paced event initiate a same-chamber refractory period and cross-chamber refractory periods in the opposite ventricle and the atrial sensing channel.

Figure 36:
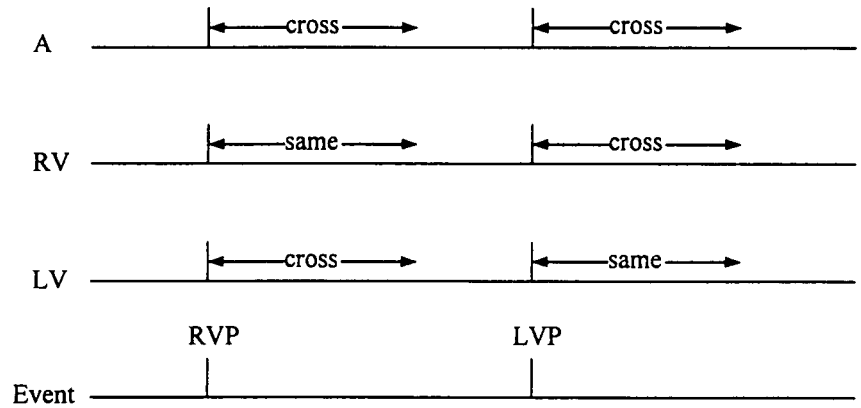
FIGS. 36-37 illustrate cross chamber and same chamber refractory periods in accordance with an embodiment of the invention.

As illustrated in the example of FIG. 36, a right ventricular pace RVP initiates a same-chamber refractory period in the right ventricle RV. The right ventricular pace RVP initiates cross-chamber refractory periods in the atrium A and the left ventricle LV. A left ventricular pace LVP initiates a same-chamber refractory period in the left ventricle LV, and cross-chamber refractory periods in the atrium and the right ventricle RV.

With biventricular pacing having positive or negative RV-LV intervals, the total sensing refractory time may be extended by the combination of same-chamber and delayed cross-chamber refractory periods. The same chamber and cross chamber refractory periods may be managed to mitigate prolonged sensing refractoriness that could compromise atrial and ventricular tachycardia detection.

Figure 37:
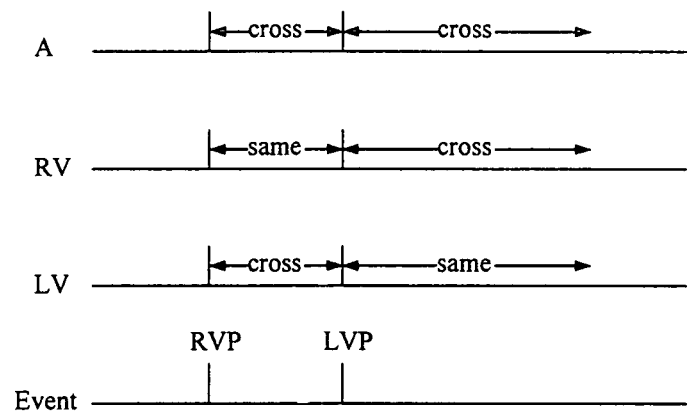

FIG. 37 illustrates an example of prolonged sensing refractoriness wherein same chamber and cross chamber refractory periods merge. A right ventricular pace is followed by a left ventricular pace producing prolonged refractoriness in all chambers.

A sensed event may initiate a same chamber refractory period to prevent oversensing in that chamber. For example, a right ventricular or left ventricular sensed event may initiate a same-chamber refractory period to prevent oversensing T-waves and far-field signals from the opposite chamber depolarization. Since many patients receiving biventricular pacing will have ventricular conduction disorders, a sensed event in one ventricle may be followed by a sensed event in the opposite ventricle only after a long delay. It is possible to avoid sensing the conducted cross-chamber event by initiating a ventricular cross-chamber refractory period for sensed ventricular events.

However, initiating a ventricular cross-chamber refractory period for sensed ventricular events may be unadvisable for some combinations of sensing and timing modes, because it creates a risk of asynchronous (competitive) pacing. For example, with RV based timing and ventricular cross-chamber refractory periods initiated by ventricular sensing, a PVC originating in the left ventricle shortly before an atrial pace can result in pacing either the left or right ventricle after the tissue refractory period, as illustrated in FIG. 38.

Figure 38:
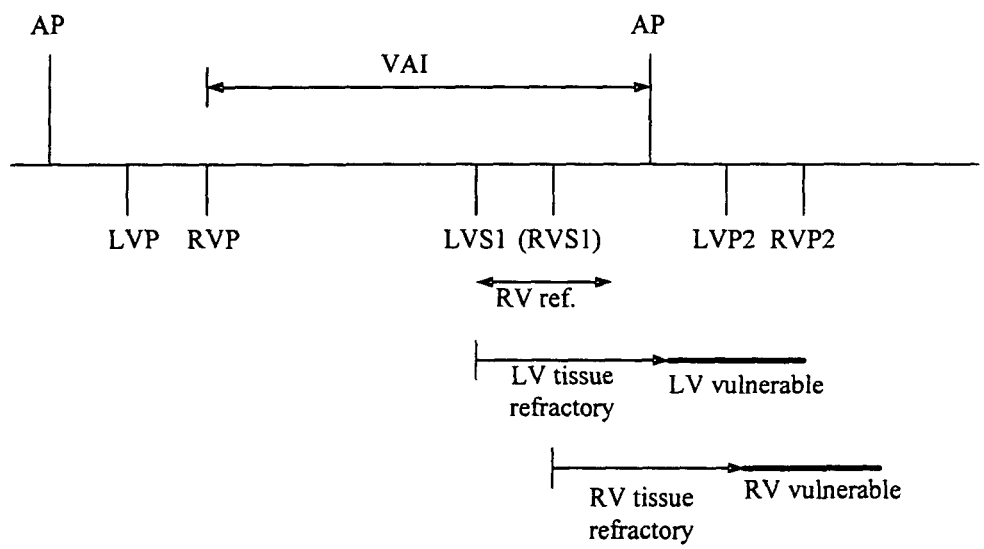
FIG. 38 is a timing diagram illustrating cross chamber refractory periods in accordance with an embodiment of the invention.

In the example of FIG. 38, right ventricular timing and a negative RV-LV interval is used. In this configuration, a right ventricular pace or sense resets VA interval VAI. A right ventricular cross chamber refractory period is initiated after a left ventricular sense LVS1. A right ventricular event is not sensed (RVS1) because it occurs within the right ventricular cross chamber refractory period RV ref. Because the right ventricular event is not sensed (RVS1), the VA interval is not reset. After the cardiac tissue recovers from tissue refractoriness, both the left ventricle and right ventricle may be paced LVP2, RVP2 during their vulnerable periods. Although in the example presented, right ventricular timing was chosen, many other similar scenarios easily can be constructed wherein the timing is based on the left ventricle or a first-in ventricular event, for example.

In DDD pacing, pacemaker inhibition has been observed in the presence of a long PR interval. A premature ventricular contraction may result in the next sinus atrial event to fall within the post ventricular atrial refractory period (PVARP). If the PVARP is long, there may be deleterious hemodynamic consequences.

Figure 39:
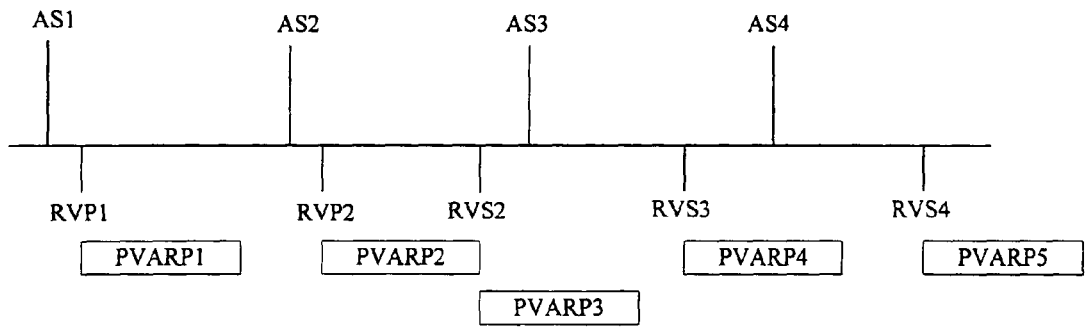
FIGS. 39-46 are diagrams illustrating implementations of PVARP in accordance with an embodiment of the invention.

In the example illustrated in FIG. 39, atrial-synchronous ventricular pacing is lost following a premature ventricular contraction. The refractory period PVARP3 initiated by the premature sensed ventricular contraction RVS2 places the next P wave AS3 within PVARP3. Because the intrinsic PR interval is long, the next atrial event AS4 falls within PVARP4 initiated by the sensed right ventricular event RVS4, thus producing abnormally delayed atrial and ventricular contractions.

In biventricular pacing therapy, loss of AV synchrony could result in failure to pace in a biventricular configuration and the patient could remain without needed resynchronization therapy for a prolonged period of time whereas constant biventricular pacing may be required. There are several mechanisms that cause such an occurrence: increasing and decreasing high atrial rates, a premature ventricular contraction (PVC), or an atrial premature contraction (APC), for example.

Figure 40:
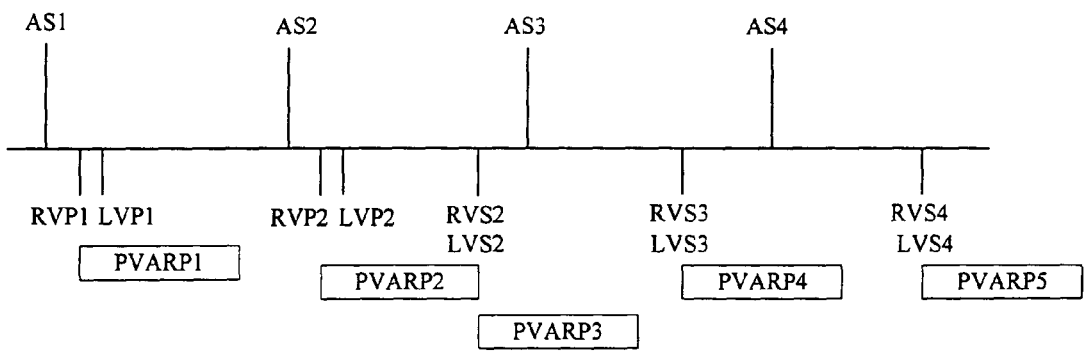

As illustrated in FIG. 40, for example, a premature ventricular contraction results in a ventricular sensed event RVS2, LVS2 and a new atrial refractory period PVARP3. The next sinus beat occurs within PVARP3 so that the next intrinsic atrial event AS3 is followed by AV conducted intrinsic ventricular events RVS3, LVS3 rather than biventricular paced events. Because the intrinsic PR interval is quite long, the intrinsic ventricular events RVS3, LVS3 occur shortly before the next sinus beat, and the intrinsic atrial contraction AS4 falls within PVARP4. Because of a persistently long intrinsic PR interval, the failure to biventricular pace is perpetuated. In this situation, the atrioventricular time may be quite prolonged and the ventricles are no longer paced in a coordinated fashion.

Loss of AV synchrony in biventricular pacing therapy may be prevented by a temporary shortening of the PVARP. Shortening of the PVARP could potentially be triggered by a persistent pattern of P wave within PVARP followed by an intrinsic R wave, for example.

Increasing and decreasing high atrial rates with a long PR interval have the potential to result in loss of AV synchrony. In biventricular pacing, the PR plus PVARP interval, denoted the intrinsic total atrial refractory period or ITARP, has important implications for upper rate behavior when intrinsic conduction is present. When the atrial rate increases so that the atrial cycle length is less than the ITARP, the next P wave would fall within the PVARP. When AV conduction is intact, the next event will be a sensed ventricular event. However, it is important that biventricular pacing for ventricular resynchronization be maintained even when intrinsic AV conduction is present.

Figure 41:
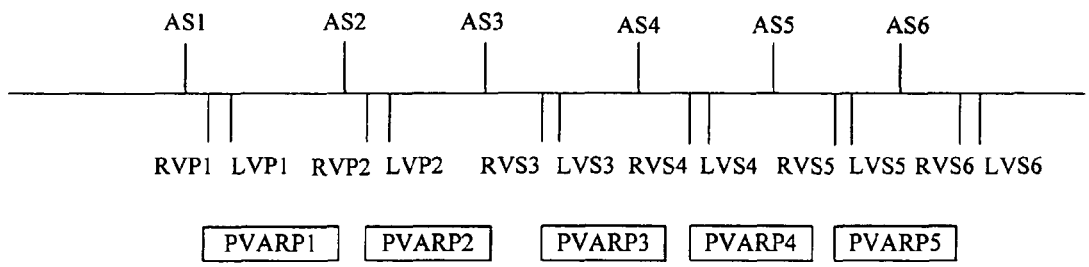

In the example of FIG. 41, a decrease in the atrial cycle length produces loss of AV synchrony. The decreasing atrial cycle length causes the intrinsic atrial event AS3 to fall within the post ventricular atrial refractory period PVARP2 initiated by RVP2. Because the intrinsic atrial event AS3 goes undetected, the intrinsic atrial contraction is followed by AV conducted intrinsic ventricular events RVS3, LVS3 rather than biventricular paced events. Because the atrial cycle length is decreasing, the next intrinsic atrial event AS4 occurs within PVARP3, perpetuating the loss of AV synchrony. Biventricular pacing will not be restored until the atrial cycle length is greater than the ITARP rate.

A similar loss of biventricular pacing occurs when the atrial rate increases above the maximum tracking rate. At the first Wenckebach beat, that is, when the atrial sense first falls in PVARP, an AV conducted intrinsic ventricular event occurs and will continue until the atrial rate decreases below the ITARP rate.

Figure 42:
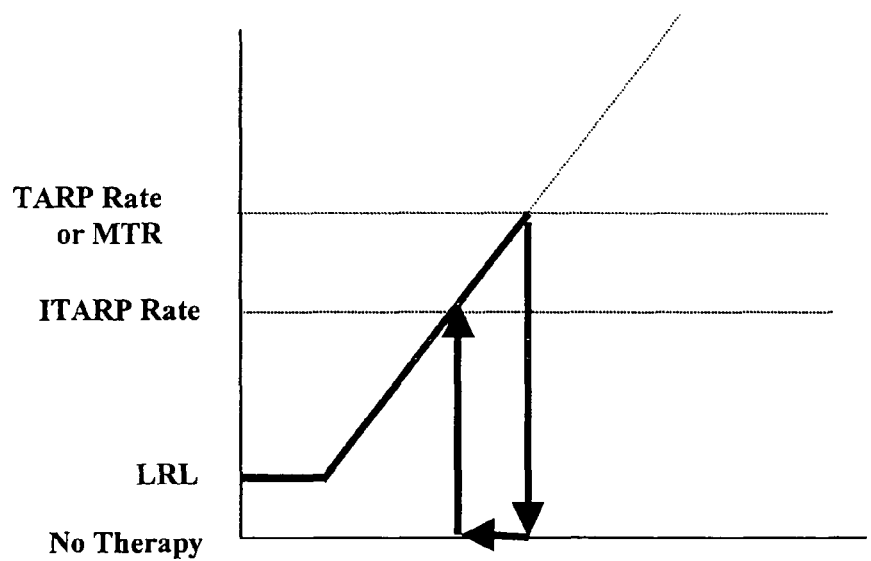

Behavior at the upper rate may be described by the graph of FIG. 42. When the atrial rate reaches the TARP (PVARP+AV) rate biventricular pacing will cease. When the atrial rate decreases to the ITARP (PVARP+PR) rate, 1:1 biventricular pacing will resume. In the graph of FIG. 42, when the atrial rate reaches TARP (PVARP+AV) biventricular pacing ceases. When the atrial falls to ITARP (PVARP+PR) biventricular pacing resumes.

The therapy hysteresis when atrial rates decrease below the MTR may be eliminated if the MTR is programmed lower than the ITARP rate. However, programming the MTR lower than the ITARP rate may have the disadvantage of too low an MTR for patient benefit. The therapy hysteresis may be mitigated using several approaches.

In one approach, a search function is used that looks for a sensed atrial event within PVARP followed by an intrinsic ventricular event. Such an event or series of repetitive events may result in one atrial sensed event being tracked, breaking the cycle.

Figure 43:
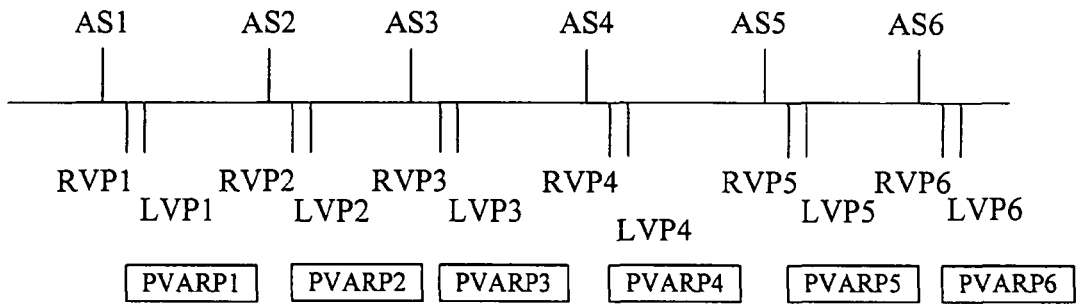

In another approach, ventricular down rate smoothing may prevent prolongation of an AS-RVS/LVS interval. Ventricular down rate smoothing to prevent the loss of biventricular pacing is illustrated in the example of FIG. 43. Although the intrinsic atrial event AS3 falls within the post ventricular atrial refractory period PVARP2, the following right and left ventricular paces RVP3, LVP3 still occur because down rate smoothing prevents the long PR from occurring. On the other hand, up rate smoothing can induce the problem by creating a prolonged AS-RVS/LVS interval.

In other approaches, minimizing or eliminating PVARP and relying on pacemaker mediated tachycardia algorithms may also prevent the loss of biventricular pacing. Another approach is to have a periodic decrease in PVARP, analogous to AV extension in DDD search hysteresis, resulting in sensing of the next P wave and resuming biventricular pacing. Furthermore, biventricular pacing may be maintained if a sensed P wave in PVARP resulted in shortening of the PVARP on the next cycle. A modification of this process would be to shorten the PVARP only for non-PVCs, i.e., a sensed ventricular event preceded by a P wave. PVARP might be eliminated except for post-PVC.

Figure 44:
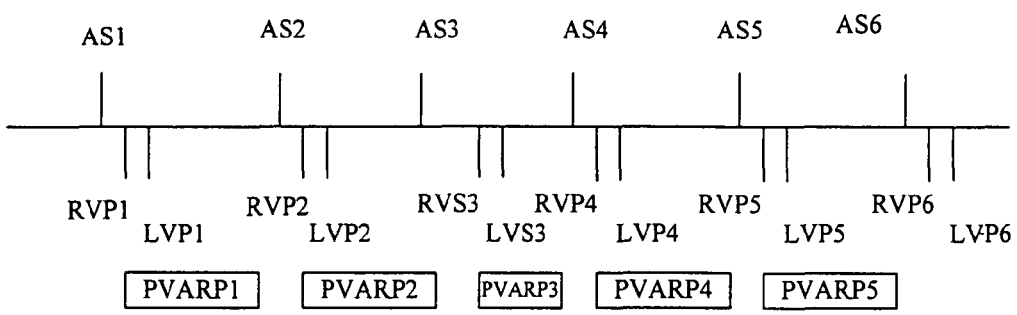

FIG. 44 illustrates shortening the PVARP to restore biventricular pacing. An intrinsic atrial event AS3 occurs within PVARP2. This situation could lead to loss of biventricular pacing because the intrinsic atrial contraction would not be followed by corresponding ventricular paces. However, according to one approach, when a P-wave is sensed within a post ventricular refractory period PVARP2, the next post ventricular refractory period PVARP3 is shortened to reestablish biventricular pacing.

Figure 45:
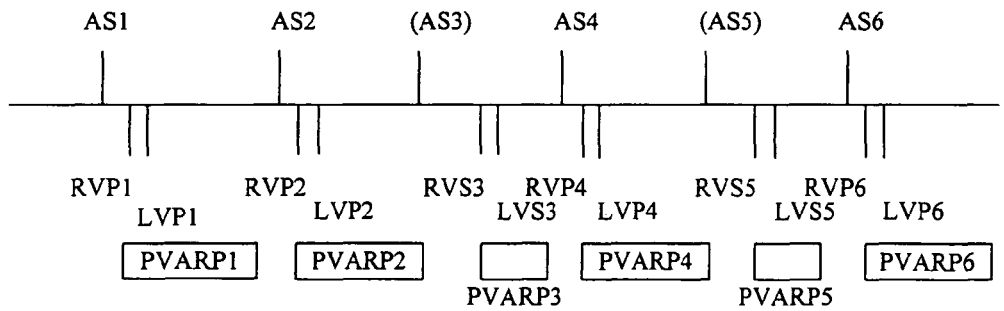

Similarly, as illustrated in FIG. 45, the post ventricular refractory period PVARP3 may be shortened only for non-PVC events, wherein the sensed ventricular contractions RVS3, LVS3 are preceded by an atrial event AS3. However, the shortening of PVARP may result in 2:1 biventricular pacing as indicated in FIG. 45. In FIG. 45, at the first Wenckebach beat, the intrinsic atrial event (AS3) falls within a post ventricular refractory period PVARP2, thereby allowing AV conducted intrinsic ventricular contractions RVS3, LVS3 to occur. The refractory period PVARP3 is shortened due to the detection of ventricular contractions RVS3, LVS3 without a corresponding sensed atrial event. The shortened refractory period PVARP3 allows the next atrial event AS4 to be sensed, and biventricular pacing of the left and right ventricles occurs RVP4, LVP4. However, the next intrinsic atrial event again falls within the refractory period PVARP4 and intrinsic AV conduction occurs with corresponding intrinsic events RVS5, LVS5.

Figure 46:
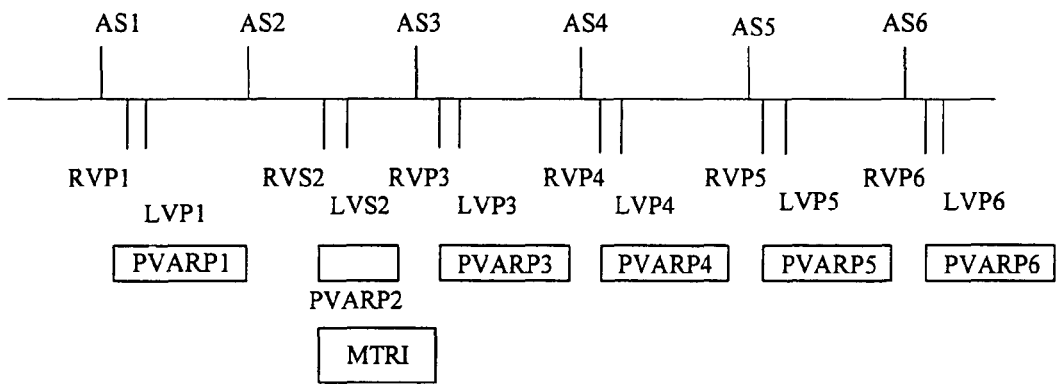

There are other methods to permit biventricular pacing at rates at or above maximum tracking rate. One can raise the maximum tracking rate as long as the R wave is intrinsic and a P wave falls within PVARP. By shortening the refractory period and decreasing the maximum tracking rate interval MTRI, biventricular pacing may be perpetuated. As illustrated in FIG. 46, the refractory period PVARP2 is shortened after the intrinsic response AS2 falls within a previous refractory period PVARP1. Also the maximum tracking rate interval is decreased allowing sensing of intrinsic atrial events and preservation of biventricular pacing.

In some situations, it is important to promote biventricular pacing rather than permit intrinsic conduction. One approach promoting biventricular pacing involves shortening a subsequent AV interval following an intrinsic ventricular event to force pacing.

Figure 47:
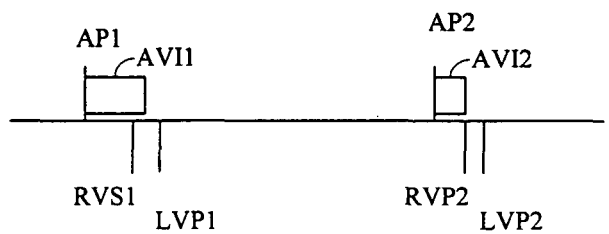
FIG. 47 is a timing diagram illustrating negative AV hysteresis in accordance with an embodiment of the invention.

Because the above approach involves shortening the AV interval, it is denoted negative AV hysteresis to distinguish it from AV hysteresis used in dual chamber pacing modes. AV hysteresis in dual chamber modes involves increasing the AV interval to allow intrinsic beats to develop. In contrast, the negative hysteresis described here involves shortening the AV interval to force pacing. If an intrinsic ventricular event (either right or left) is sensed within the AV interval, the subsequent AV interval is shortened, forcing pacing. This approach is illustrated in FIG. 47. In this example, a right ventricular event is sensed RVS1 within the programmed AV interval AVI1. On the next cardiac cycle beginning with AP2, the AV interval AVI2 is shortened, producing biventricular pacing RVP2, LVP2.

Another approach to maintaining biventricular pacing mitigates the effects of variable conduction delay between the right and left ventricles. In this approach, denoted negative biventricular hysteresis, even if the first ventricular event is a paced one, the second ventricular event may be intrinsic due either to conduction from the atrium or conduction from the opposite ventricle. In this case, the subsequent RV-LV interval is shortened.

Figure 48:
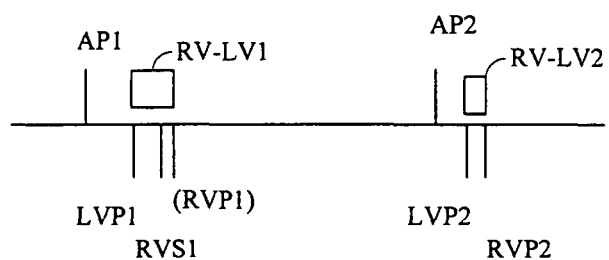
FIG. 48 is a timing diagram illustrating dynamic RV-LV interval in accordance with an embodiment of the invention.

Biventricular hysteresis is illustrated in the diagram of FIG. 48. In this example, the first programmed RV-LV interval RV-LV1 is preempted by an intrinsic right ventricular event RVS1 following the left ventricular pace LVP1. Therefore, the right ventricular pace scheduled to occur following the programmed RV-LV interval is inhibited (RVP1). On the next cardiac cycle, the RV-LV interval RV-LV2 is shortened so that both the left ventricle and the right ventricular are paced LVP2, RVP2.

In some cases, it may be desirable that the RV-LV interval be dynamic. It may respond to the rate, activity, or to the previous cycle or to a combination of these factors, for example. Thus, under various conditions, the RV-LV interval may be changed. For example, a rate-adaptive RV-LV interval might shorten as the sensor-detected activity increases or as the intrinsic heart rate increases.

Biventricular pacing during atrial fibrillation may present a challenge, particularly at rapid ventricular rates. One approach is to maintain biventricular pacing during atrial fibrillation by overdrive pacing during atrial fibrillation, permitting biventricular capture rather than conduction. Another approach is to use a biventricular triggered mode, triggering opposite chamber pacing off of an RV sense, an LV sense, or both. For example, with biventricular sensing, one might trigger off the earlier of either RV sense or LV sense.

Figure 49:
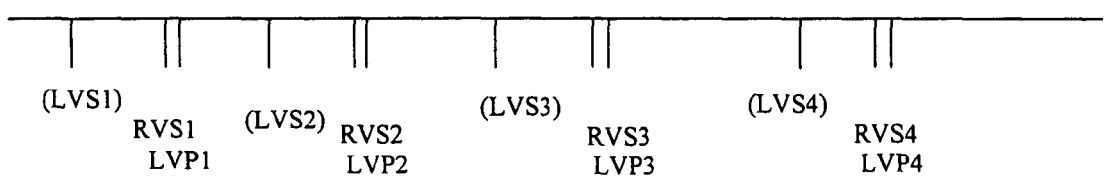
FIG. 49 is timing diagram illustrating asynchronous pacing.

Asynchronous pacing may occur when triggering with RV-only or LV-only sensing. For example, as illustrated in FIG. 49, with RV-only sensing, if an undetected LV sensed event occurs first, the RV sense may occur after a long conduction delay and a triggered LV pace may be delivered after LV refractoriness has recovered. With any sensing mode, it is important to limit the maximum triggering rates when applying biventricular triggering to atrial fibrillation.

Other methods of cardiac rhythm management for synchronized pacing of the heart are described in U.S. Pat. Nos. 6,574,506, 6,829,505, and 6,553,258, all commonly owned and filed on Jun. 27, 2002 and which are hereby incorporated by reference herein in their respective entireties.

According to a method described in U.S. Pat. No. 6,574,506, a rate chamber and a synchronized chamber are sensed through separate channels and a pace is delivered at a specified pacing instant defined with respect to expiration of a rate chamber escape interval based on rate chamber events. The chamber-based method of pacing timing using sensed rate and synchronized chambers described in U.S. Pat. No. 6,574,506 may be enhanced by the event-based timing cycle methods of the present invention.

A method described in U.S. Pat. No. 6,829,505 involves cardiac pacing using sensed rate and synchronized chambers in conjunction with the use of a synchronized chamber protection period triggered by intrinsic activity in the synchronized chamber. The methods of synchronized pacing and particularly the methods of establishing a pacing protection interval may be enhanced by the use of the present invention to include pacing modes that are event-based and to include pacing protection intervals that may be established for either chamber.

U.S. Pat. No. 6,553,258 describes methods for managing refractory periods in connection with biventricular or biatrial pacing. The methods described in U.S. Pat. No. 6,553,258 may be enhanced to include the multisite pacing techniques described herein.

Methods for delivering cardiac therapy to improve the hemodynamic efficiency of a heart by simultaneously pacing both ventricles are described in commonly owned U.S. Pat. No. 4,928,688 which is hereby incorporated herein by reference in its entirety. The methods of pacing described in U.S. Pat. No. 4,928,688 may be enhanced, for example, by the methods described above for identifying a group of cardiac events associated with a depolarization wavefront and delivering pacing therapy based on at least one cardiac event of the group.

Various modifications and additions can be made to the preferred embodiments discussed above without departing from the scope of the present invention. Accordingly, the scope of the present invention should not be limited by the particular embodiments described above, but should be defined only by the claims set forth below and equivalents thereof.

What is claimed is:

1. A method for operating a cardiac rhythm management device to deliver pacing pulses to a heart, comprising:
    sensing for an electrical depolarization of a right ventricle during a cardiac cycle through a right ventricular sensing channel;
    sensing for an electrical depolarization of a left ventricle during the cardiac cycle through a left ventricular sensing channel;
    initiating the VA pacing escape interval for the cardiac cycle relative to a determined first in time sensed ventricular depolarization for the cardiac cycle when sensing both a left ventricular depolarization and a separate right ventricular depolarization for the cardiac cycle, wherein the determined first in time sensed ventricular depolarization comprises either the sensed right ventricular depolarization or the sensed left ventricular depolarization; and
    delivering pacing for the cardiac cycle using the VA pacing escape interval.

2. The method of claim 1, further comprising initiating the VA pacing escape interval relative to a first paced ventricle for ventricular paced cardiac cycles.

3. The method of claim 2, further comprising delivering pacing to both the right ventricle and the left ventricle during the ventricular paced cardiac cycles.

4. The method of claim 1, including:
    inhibiting a scheduled ventricular pace to either the left ventricle or right ventricle when sensing a depolarization in the either of the left ventricle or right ventricle; and
    initiating the VA pacing escape interval from a time of the inhibited scheduled ventricular pace.

5. The method of claim 1, including triggering delivery of a ventricular pace to either of the left ventricle or right ventricle when sensing a depolarization in the other of the left ventricle or right ventricle.

6. The method of claim 1, including initiating an interventricular pace delay value from the right ventricle to the left ventricle when sensing a depolarization in the either of the left ventricle or right ventricle, wherein the interventricular pace delay value from the right ventricle to the left ventricle is a negative value.

7. A cardiac rhythm management device, comprising:
    sensing circuitry configured to sense electrical depolarizations of a right ventricle and a left ventricle including:
        a left ventricular sensing channel configured to sense for left ventricular depolarizations, and
        a right ventricular sensing channel configured to sense for right ventricular depolarizations;
    timing circuitry configured to time a ventriculo-atrial (VA) pacing escape interval for each cardiac cycle, the VA pacing escape interval initiated relative to a determined first in time sensed ventricular depolarization for the cardiac cycle when both a left ventricular depolarization and a separate right ventricular depolarization are sensed for the cardiac cycle, wherein the determined first in time sensed ventricular depolarization comprises either the sensed right ventricular depolarization or the sensed left ventricular depolarization; and pacing controller circuitry configured to deliver pacing using the VA pacing escape interval.

8. The device of claim 7, wherein the timing circuitry is configured to initiate the VA pacing escape interval relative to a first paced ventricle for ventricular paced cardiac cycles.

9. The device of claim 7, wherein the pacing controller is configured to inhibit a scheduled ventricular pace to either the left ventricle or right ventricle when a depolarization in the either of the left ventricle or right ventricle is sensed; and wherein the timer circuitry is configured to initiate the VA pacing escape interval from a time of the inhibited scheduled ventricular pace.

10. The device of claim 7, wherein pacing controller circuitry is configured to trigger delivery of a ventricular pace to either of the left ventricle or right ventricle when sensing a depolarization in the other of the left ventricle or right ventricle.

11. The device of claim 7, wherein timer circuitry is configured to initiate an interventricular pace delay value from the right ventricle to the left ventricle when sensing a depolarization in the either of the left ventricle or right ventricle, wherein the interventricular pace delay value from the right ventricle to the left ventricle is a negative value.

* * * * *